(12) United States Patent
Milella, Jr.

(10) Patent No.: US 9,681,962 B2
(45) Date of Patent: Jun. 20, 2017

(54) IN-SITU FORMED SPINAL IMPLANT

(71) Applicant: Michael J. Milella, Jr., Johns Creek, GA (US)

(72) Inventor: Michael J. Milella, Jr., Johns Creek, GA (US)

(*) Notice: Subject to any disclaimer, the term of this patent is extended or adjusted under 35 U.S.C. 154(b) by 55 days.

(21) Appl. No.: 14/722,268

(22) Filed: May 27, 2015

(65) Prior Publication Data
US 2015/0265421 A1    Sep. 24, 2015

Related U.S. Application Data

(62) Division of application No. 13/758,020, filed on Feb. 4, 2013, now Pat. No. 9,060,870.

(60) Provisional application No. 61/595,091, filed on Feb. 5, 2012.

(51) Int. Cl.
| | |
|---|---|
| *A61F 2/46* | (2006.01) |
| *A61F 2/44* | (2006.01) |
| *A61F 2/28* | (2006.01) |
| *A61F 2/30* | (2006.01) |

(52) U.S. Cl.
CPC ........... *A61F 2/4611* (2013.01); *A61F 2/442* (2013.01); *A61F 2/4465* (2013.01); *A61F 2002/2835* (2013.01); *A61F 2002/3008* (2013.01); *A61F 2002/30131* (2013.01); *A61F 2002/30293* (2013.01); *A61F 2002/30772* (2013.01); *A61F 2002/30841* (2013.01); *A61F 2220/0016* (2013.01); *A61F 2230/0069* (2013.01); *A61F 2230/0091* (2013.01)

(58) Field of Classification Search
CPC . A61F 2/442; A61F 2002/4415; A61F 2/4611
See application file for complete search history.

(56) References Cited

U.S. PATENT DOCUMENTS

| | | |
|---|---|---|
| 7,503,920 B2 | 3/2009 | Siegal |
| 7,666,227 B2 | 2/2010 | Schaller |
| 7,670,374 B2 | 3/2010 | Schaller |
| 7,670,375 B2 | 3/2010 | Schaller |
| 7,731,751 B2 | 6/2010 | Butler et al. |
| 7,785,368 B2 | 8/2010 | Schaller |
| 7,857,857 B2 | 12/2010 | Kim |
| 7,947,078 B2 | 5/2011 | Siegal |

(Continued)

OTHER PUBLICATIONS

Luis M. Rosales Olivarez et al., "First Clinical Experience with an Innovative Vertebral Augmentation Device for Painful Vertebral Coimpression Fractures", Benvenue Medical, Kiva VCF Treatment System, Jun. 2009, pp. 1-8.

*Primary Examiner* — David Bates
*Assistant Examiner* — Olivia C Chang
(74) *Attorney, Agent, or Firm* — Greer, Burns & Crain, Ltd.

(57) ABSTRACT

An in-situ formed spinal implant is provided, including an elongate strip having a proximal end and an opposite distal end, the strip having a plurality of spaced teeth disposed along edges of the strip. The strip has a generally arcuate or concave cross-section and is configured for being coiled into a spiral from the proximate end to the distal end for placement between adjacent spinal vertebrae, such that upon formation of the coiled shape, the teeth on a first edge engage one of the vertebrae, and teeth of an opposite, second edge engage the other of the vertebrae.

13 Claims, 38 Drawing Sheets

(56) References Cited

U.S. PATENT DOCUMENTS

| | | |
|---|---|---|
| 8,057,544 B2 | 11/2011 | Schaller |
| 8,197,548 B2 | 6/2012 | Sack et al. |
| 2004/0225361 A1 | 11/2004 | Glenn et al. |
| 2004/0230309 A1 | 11/2004 | Dimauro et al. |
| 2007/0067035 A1 | 3/2007 | Falahee |
| 2007/0093906 A1 | 4/2007 | Hudgins et al. |
| 2007/0270952 A1 | 11/2007 | Wistrom et al. |
| 2008/0119853 A1 | 5/2008 | Felt et al. |
| 2008/0140207 A1 | 6/2008 | Olmos et al. |
| 2008/0208255 A1 | 8/2008 | Siegal |
| 2008/0221687 A1* | 9/2008 | Viker .................... A61F 2/4455 623/17.16 |
| 2008/0234732 A1 | 9/2008 | Landry et al. |
| 2008/0236601 A1 | 10/2008 | Jacobus |
| 2008/0294171 A1 | 11/2008 | Boehm, Jr. |
| 2008/0312743 A1* | 12/2008 | Vila ....................... A61F 2/442 623/17.16 |
| 2009/0112323 A1 | 4/2009 | Hestad et al. |
| 2009/0234454 A1 | 9/2009 | Siegal |
| 2010/0010634 A1 | 1/2010 | Binotto |
| 2010/0168798 A1 | 7/2010 | Clineff et al. |
| 2010/0170521 A1 | 7/2010 | Gall |
| 2010/0198263 A1 | 8/2010 | Siegal et al. |
| 2010/0262147 A1 | 10/2010 | Siegal et al. |
| 2011/0009970 A1 | 1/2011 | Puno |
| 2011/0077740 A1 | 3/2011 | Perez-cruet et al. |
| 2011/0118789 A1 | 5/2011 | Siegal |
| 2011/0238072 A1 | 9/2011 | Tyndall |
| 2011/0264146 A1 | 10/2011 | Siegal |
| 2013/0110239 A1* | 5/2013 | Siegal ................ A61B 17/7098 623/17.16 |

\* cited by examiner

SECTION A-A

SECTION A-A

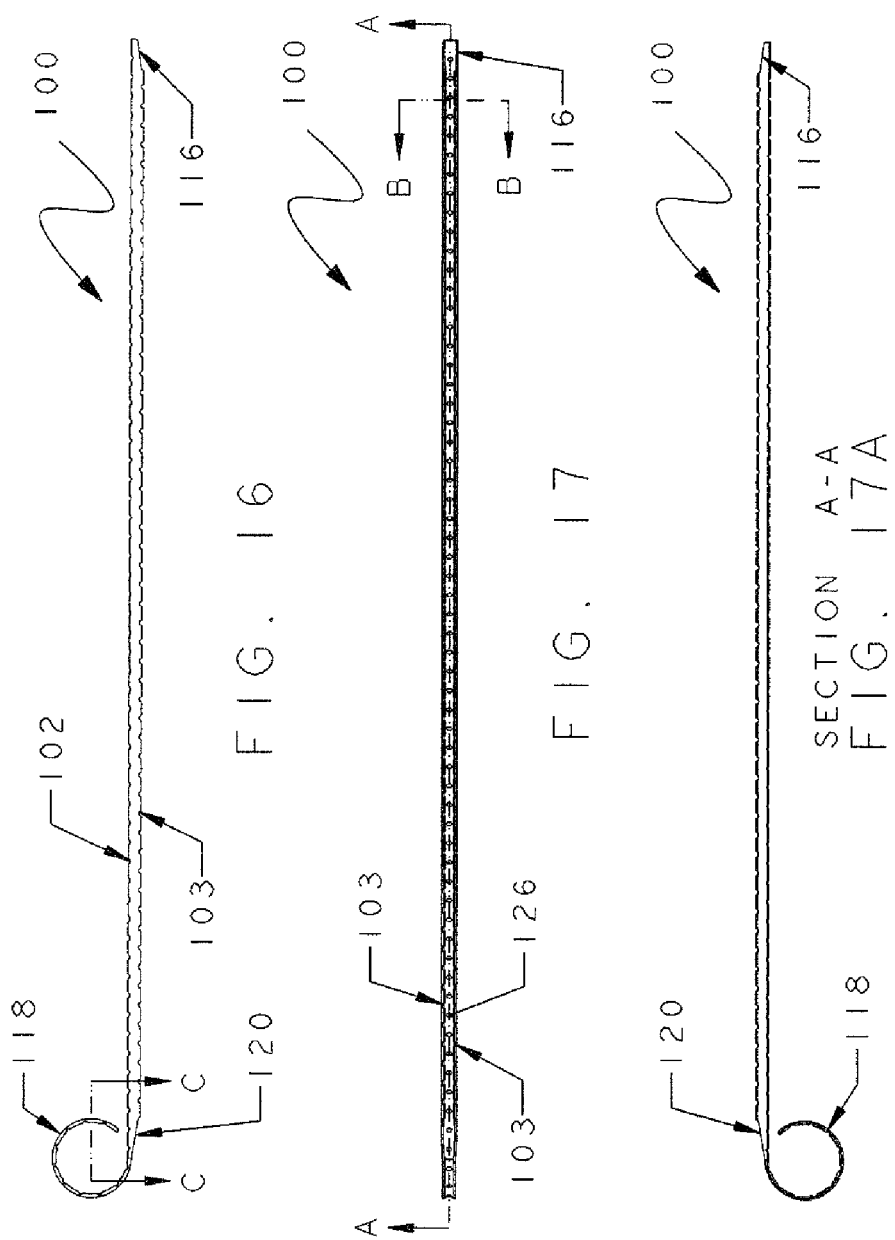

SECTION A-A

SECTION B-B

SECTION C-C

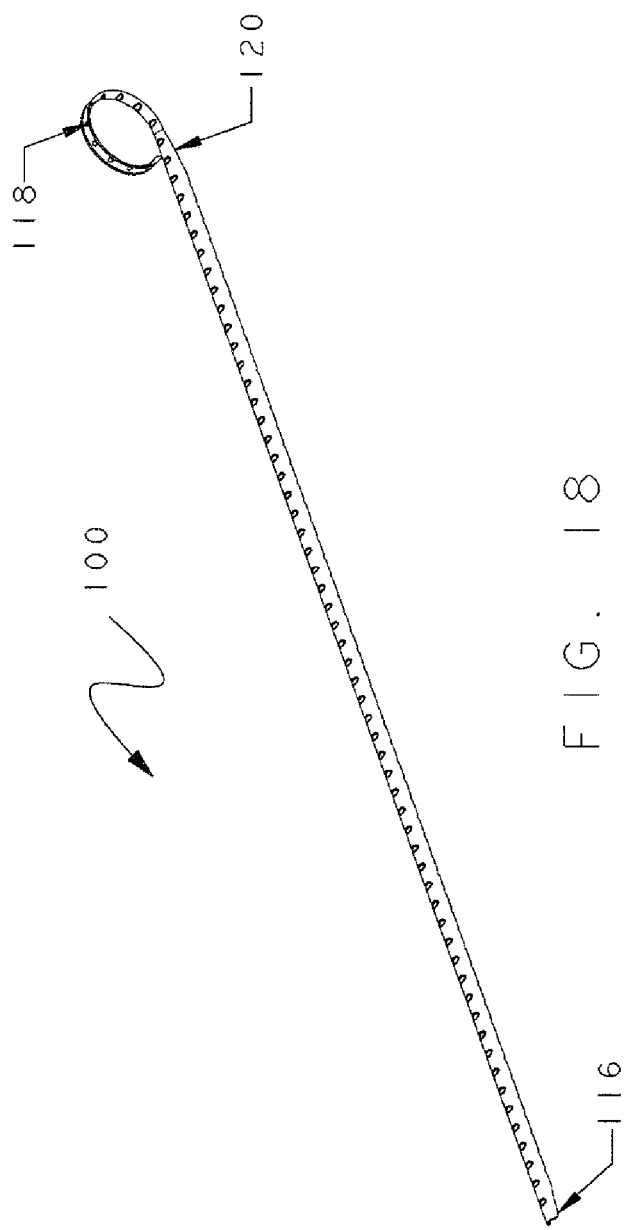

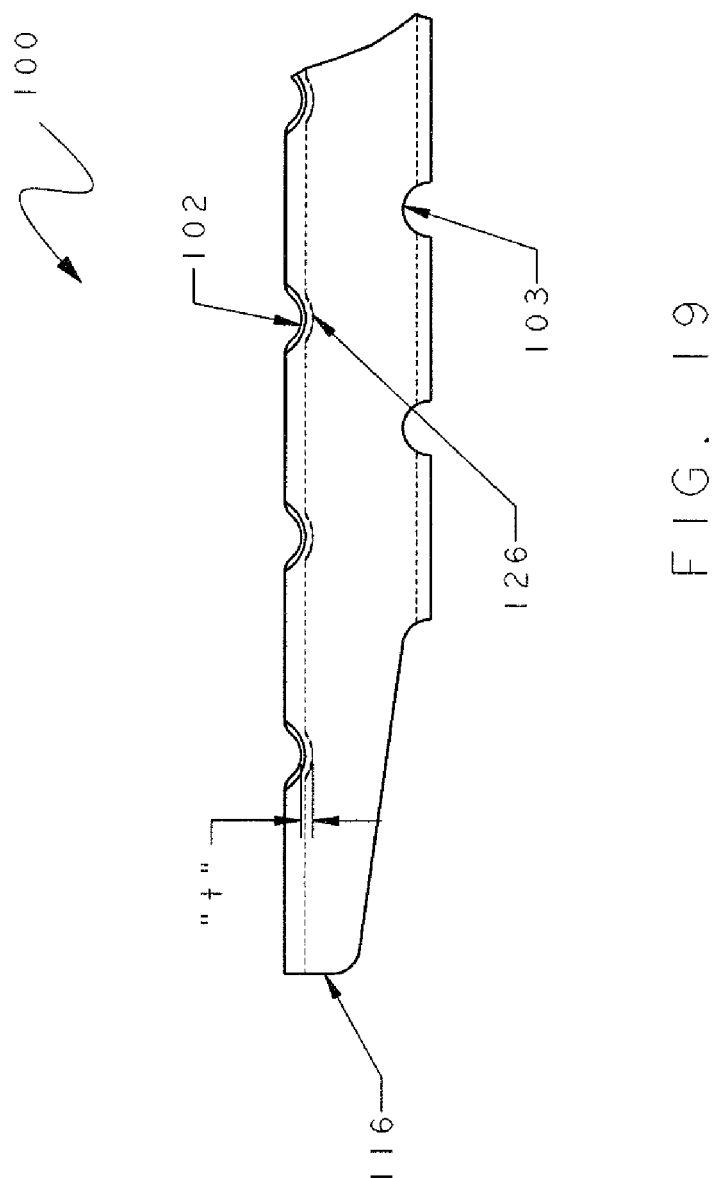

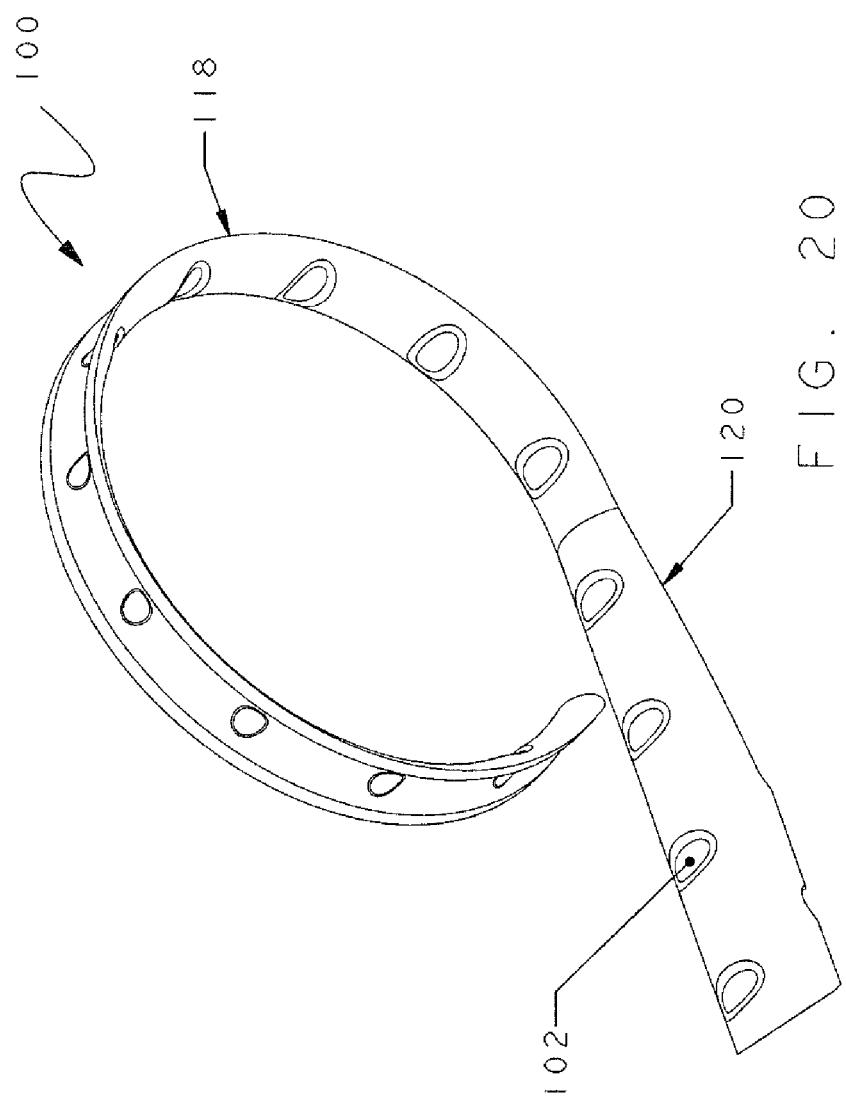

SECTION D-D

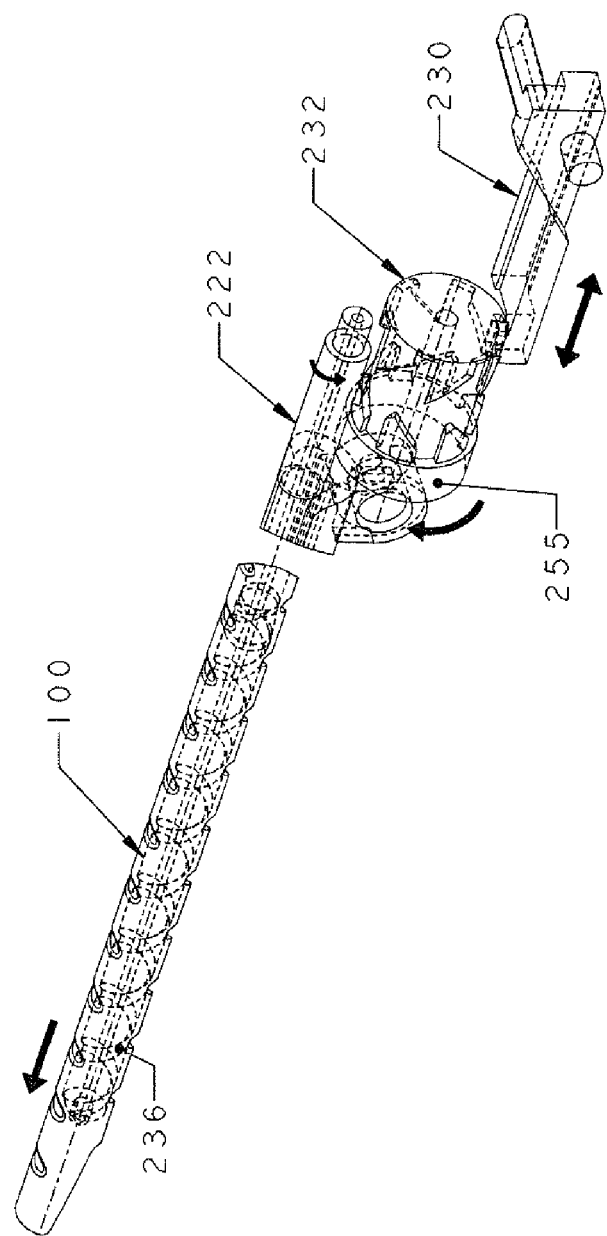

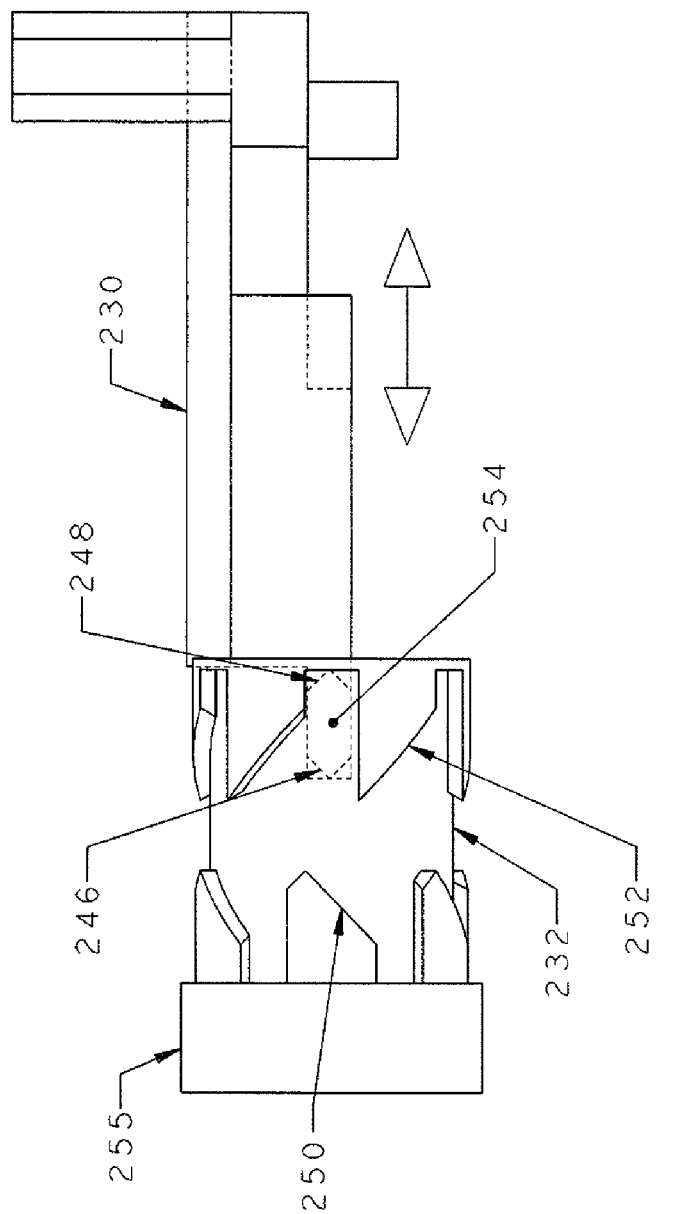

IN-SITU FORMED SPINAL IMPLANT

RELATED APPLICATIONS

This application is a divisional of, and claims 35 USC 120 priority from U.S. Ser. No. 13/758,020, filed Feb. 4, 2013 and also priority under 35 USC 119(e) base on U.S. Provisional Application Ser. No. 61/595,091 filed Feb. 5, 2012.

BACKGROUND

The present invention relates generally to the field of spinal fusion or arthrodesis, as well as fracture repairs in cases of trauma or osteoporosis, and prosthetic replacement of a spinal joint, particularly relating to installation of a spinal repair device or system of such devices through minimally invasive methods.

Conventional spinal repair devices require an open installation procedure, which increases patient recovery times and increases tissue disruption at and around the incision site. In the case of spinal fusion or arthrodesis, the surgeon typically uses a "cage", spacer, or an interbody device that distracts the disc space to normal heights. The conventional device aids in fusion of the vertebral bodies by providing an area within the device that can be packed with bone or artificial material creating scaffolding for bone growth. The surgical site is opened sufficiently to allow for preparation of the disc and vertebral bodies, and to allow implantation of the device.

One drawback of conventional devices of this type is that in order to increase stability, the device must be sufficiently sized in order to maximize bone contact area or endplate coverage of the vertebral bodies. It is also desired that the frontal area of the device is minimized in order to reduce the size of the incision. Since the devices are usually rectangular, trapezoidal, or cylindrical in shape, and the height is determined by the desired disc height of the patient, devices with a larger frontal area must be used in order to maximize bone contact area, requiring the surgeon to create a larger incision in order to install the device.

Conventional devices also have varying tooth profiles or orientation sensitive geometry that helps prevent expulsion of the device while fusion takes place. This geometry is typically oriented such that the tooth profile doesn't interfere with the installation of the device, and will reduce the possible expulsion of the device when forces are applied. This requires the surgeon to place the device in a specific location on the body such that the orientation of the device is accomplished for preventing expulsion.

To those persons skilled in the art, the features, elements, and objects of the present spine repair device will become apparent after reading the details as described below.

SUMMARY

The above-identified needs are met by the present implant, which is preferably delivered or installed thru a small cannula and deployed percutaneously such that it has greater bone contact area than conventional devices, small frontal area for smaller incisions, omni-directional tooth profiles for preventing expulsion, and an increased height from its pre-deployed state. It is contemplated that the present implant and alternate embodiments are manufactured from materials such as polyetheretherketone (PEEK), titanium alloy, carbon fiber, or stainless steel. It is also contemplated that alternate embodiments of the present implant and alternate systems are manufactured from shape memory alloys and shape memory polymers allowing the device to conform more closely to the anatomical shape of the body.

The present implant or system of devices can be delivered through a small diameter cannula and deployed intradiscal for use as an interbody fusion device, deployed within the cancellous portion of the fractured vertebral body in order to repair vertebral compression fractures, and as a reduced invasive disc replacement when used in conjunction with alternate systems of the present implant. Systems of the present implant include implantable fusion devices of varying length and heights for use in fusion, systems of various heights and sizes and materials for use in joint prosthesis, and systems that allow the delivery of natural or artificial materials for use in filling a void within a joint. The system also includes instrumentation to deliver the implant or system of devices.

More specifically, an in-situ formed spinal implant is provided, including an elongate strip having a proximal end and an opposite distal end, the strip having a plurality of spaced teeth disposed along edges of the strip. The strip has a generally arcuate or concave cross-section and is configured for being coiled into a spiral from the proximate end to the distal end for placement between adjacent spinal vertebrae, such that upon formation of the coiled shape, the teeth on a first edge engage one of the vertebrae, and teeth of an opposite, second edge engage the other of the vertebrae.

In another embodiment, a device is provided for installing a coiled elongate strip as a spinal implant. The device includes a housing having a delivery tube at one end, and an implant loading chamber at an opposite end. A trigger-operated indexing mechanism associated with the housing moves the strip from the loading chamber to the delivery tube. A deployment tip is disposed at an end of the delivery tube, the deployment tip including a flared ramp for changing the concavity of the strip. A tensioning cord is disposed at the deployment tip and forms a loop for causing the strip to form a coiled spiral upon progressive movement from the delivery tube.

BRIEF DESCRIPTION OF THE DRAWINGS

FIG. 10A is a horizontal cross-section taken along the line B-B of FIG. 10 and in the direction indicated generally;

FIG. 16 is a side plan view of the present implant pre-deployment;

FIG. 17 is a front plan view of the present implant pre-deployment;

FIG. 17A is a horizontal cross-section taken along the line A-A of FIG. 17 and in the direction indicated generally;

FIG. 18 is an isometric view of the present implant pre-deployment;

FIG. 19 is an enlarged fragmentary side view of the distal end of the present implant pre-deployment;

FIG. 20 is an enlarged isometric view of the proximal end of the present implant pre-deployment;

FIG. 32 is an isometric view of the implant delivery device of FIG. 25 with components removed for clarity; and FIG. 32A is a bottom plan view of the implant delivery device of FIG. 25 with components removed for clarity of the implant delivery device.

DETAILED DESCRIPTION

Figure 1:
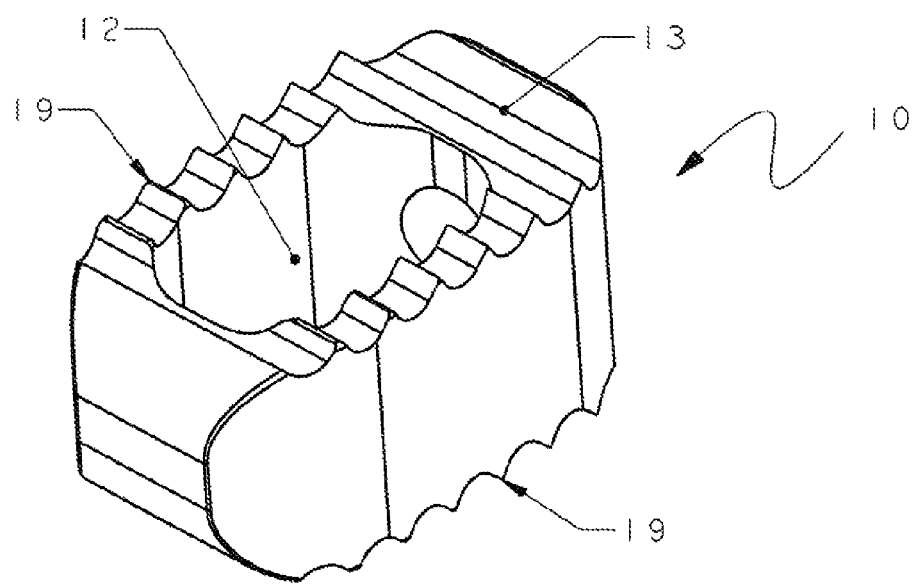
FIG. 1 is an isometric view of a prior art cage.
Figure 2:
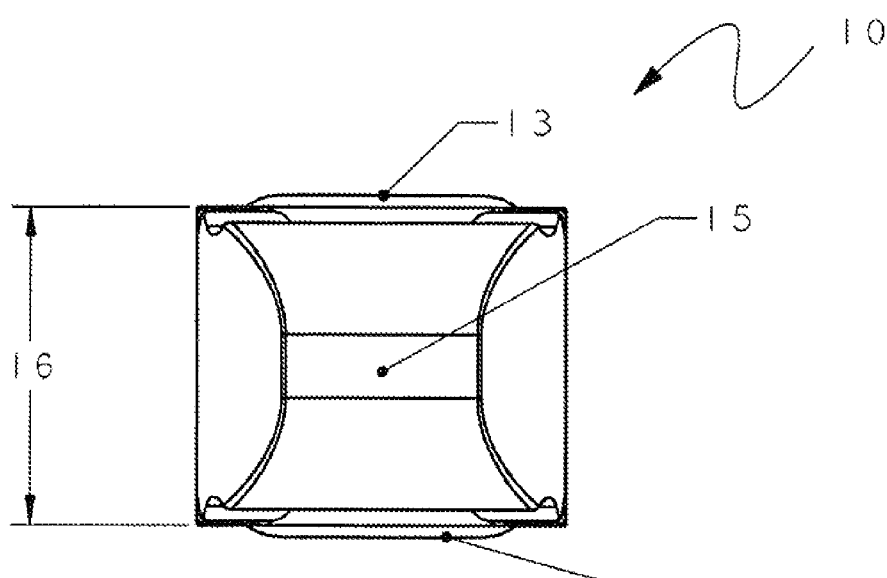
FIG. 2 is a front plan view of the prior art cage of FIG. 1.
Figure 3:
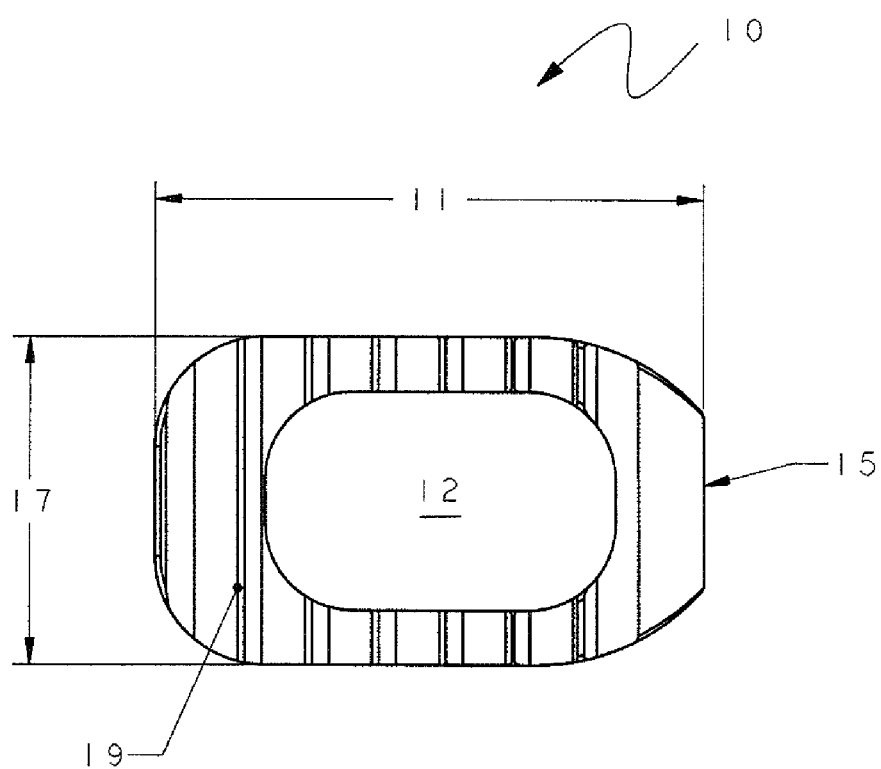
FIG. 3 is a top plan view of the prior art cage of FIG. 1.
Figure 4:
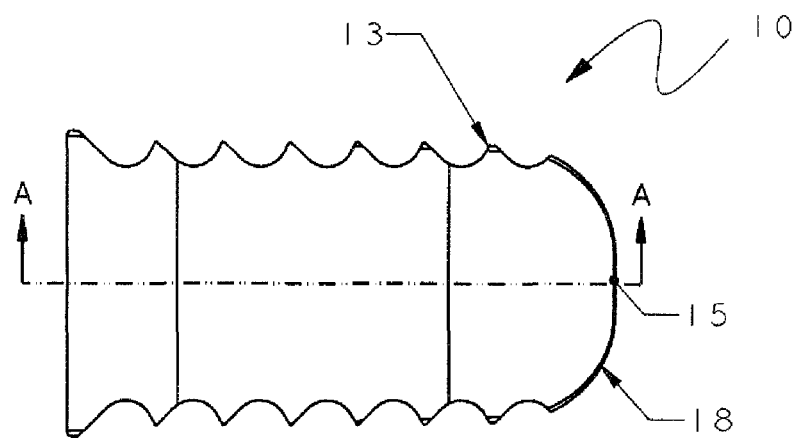
FIG. 4 is a side plan view of the prior art cage of FIG. 1.
Figure 4A:
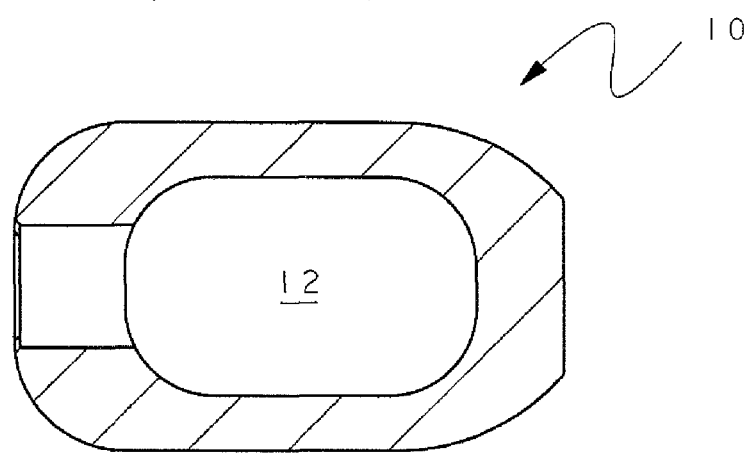
FIG. 4A is a horizontal cross-section taken along the line A-A of FIG. 4 and in the direction generally indicated.
Figure 5:
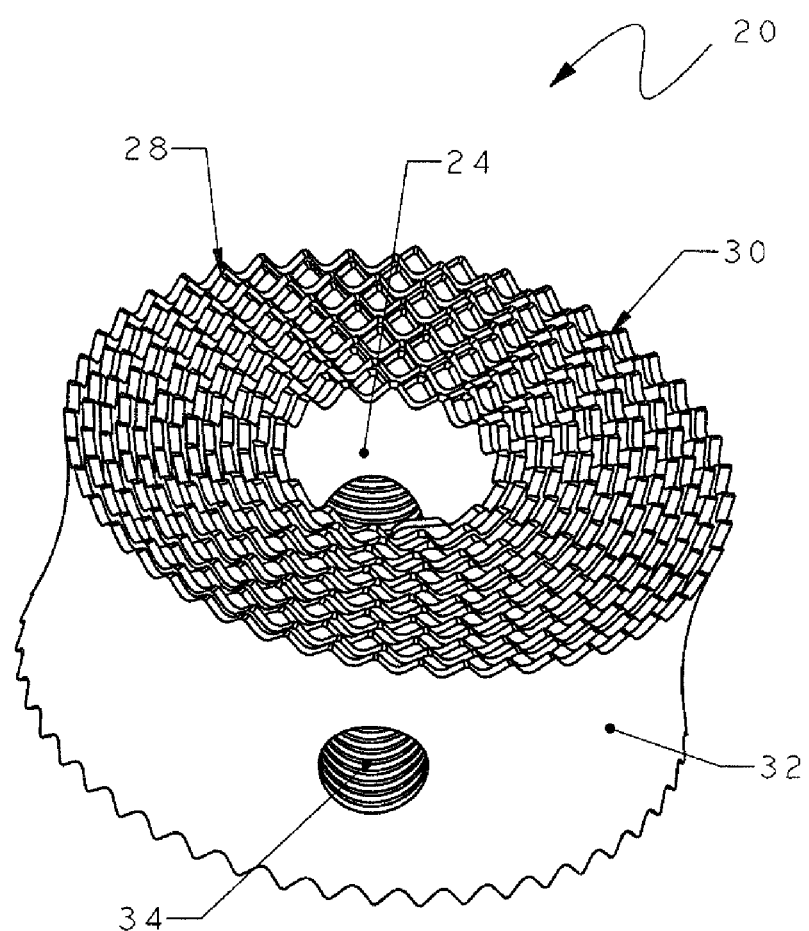
FIG. 5 is an isometric view of the present implant post-deployment.
Figure 6:
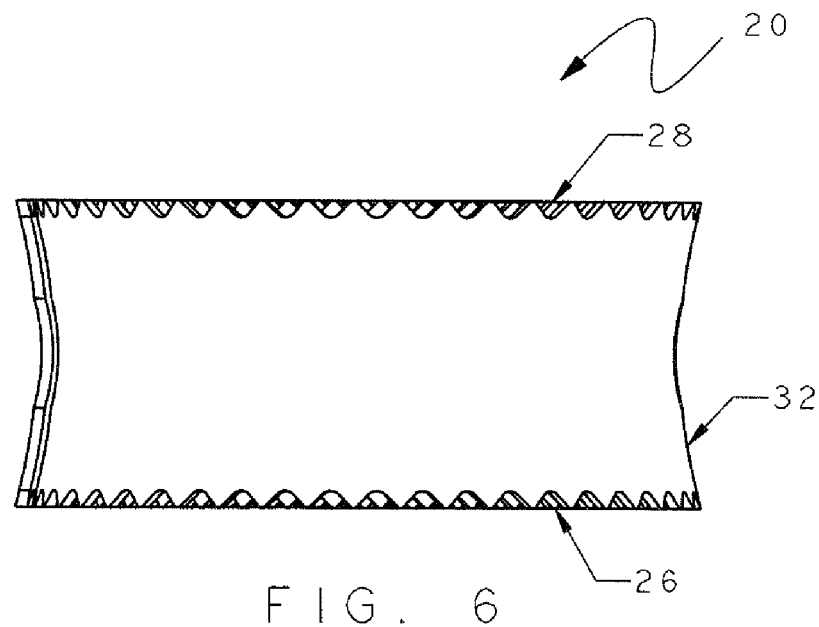
FIG. 6 is a front plan view of the present implant post-deployment.
Figure 7:
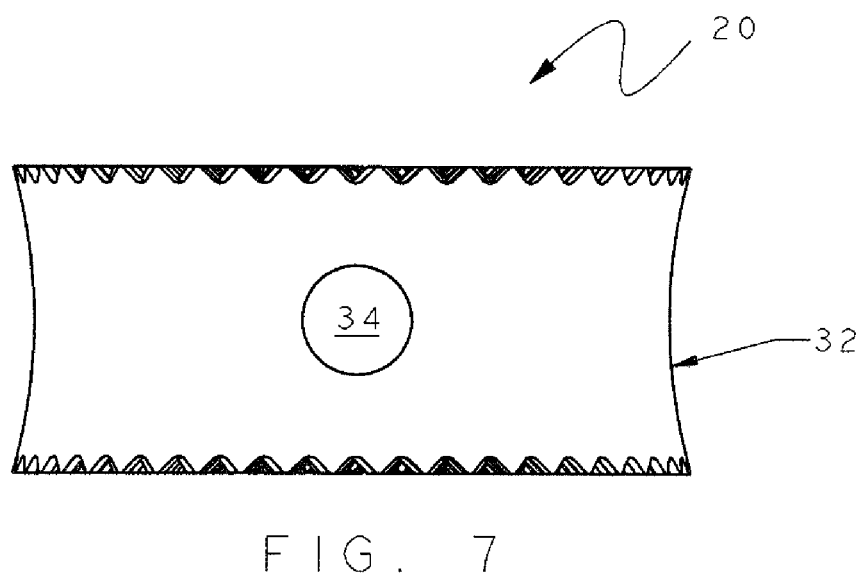
FIG. 7 is a side view of the present implant post-deployment.

Referring to FIGS. 1-4A, a prior art implant is shown and generally designated 10, particularly designed for use as in spinal fusion or arthrodesis. However, it is contemplated that the present implant is suitable for use with other types of surgical procedures including, vertebral compression fractures, and as a minimally invasive disc replacement, or the like. The device 10 is preferably machined from bar stock; however other fabrication techniques are contemplated including injection molding. The materials used to manufacture the device 10 include polyetheretherketone (PEEK), titanium alloy, ceramic, bone, carbon fiber, or stainless steel, as is known in the art.

More specifically, the prior art implant 10 typically includes six sides and an opening defining a passage 12 between upper and lower surfaces, respectively 13 and 14. The passage 12 is generally packed with bone or other natural or artificial materials for use in promoting fusion between an upper and lower vertebral body. At least one end 15 has a reduced frontal area as defined by dimensions 16 and 17 and a radiused edge 18, and is provided for ease of insertion. As is known in the art, the upper surface 13 and lower surface 14 are usually populated with geometry or teeth 19 used to increase pressure on the endplate of the vertebral body and prevent expulsion. A portion of at least one of the surfaces 13 and 14 is formed flat or on a lordotic angle, in order to more anatomically conform to the endplate of the vertebral body. The lower surface 14 is sized to match the height as required by the anatomical disc height of the patient, and area as defined by dimensions 11 and 17 is increased in order to enhance stability of the spinal column.

Referring now to FIGS. 5-10A, the present implant in the post-deployed state is generally designated 20. A main difference between the implants 10 and 20 is that, instead of a solid shape, the present implant 20 is fabricated of an elongate strip formed into a thin walled spiral 22 wound such that it forms a generally cylindrical shape with a passage 24 located at the centroid or vertical axis of the spiral 22. The present implant 20 is configured for deployment in such a manner that both the passage 24 and a diametrical dimension 25 can be controlled and more closely matched with the anatomical features of the patient. A lower surface or first edge 26, and an upper surface or second edge 28 are populated with geometry or teeth 30 used to increase pressure on the endplate of the vertebral body and prevent expulsion. Walls 32 are concave and nest within each other to provide greater stability of the implant 20. It is contemplated that symmetric and asymmetric curved and segmented shapes, both regular and irregular, are suitable for the walls 32.

An opening 34 is preferably cylindrical or circular in horizontal cross-section, but it is contemplated that other shapes are also suitable, including but not limited to oval, triangular, square, pentagonal, hexagonal and other configurations of polygonal shapes, both regular and irregular. The opening 34 is used post-deployment in order to introduce bone or other natural or artificial materials into the passage 24, and is formed by a linearly spaced plurality of holes disposed along wall 32 of the elongate strip 20. In other configurations, multiple openings can be located along the wall 32 to provide access to the passage 24.

While other materials are contemplated, is preferred that the present implant 20 is manufactured from materials such as polyetheretherketone (PEEK), titanium alloy, carbon fiber, or stainless steel. It is also contemplated that alternate embodiments of the present implant and alternate systems are manufactured from shape memory alloys and shape memory polymers allowing the device to conform more closely to the anatomical shape of the body. For non-metallic or ferrous materials, radio-opaque stripes are placed along the length of the pre-deployed device to provide the surgeon feedback regarding the amount of implant currently deployed.

Figure 11:
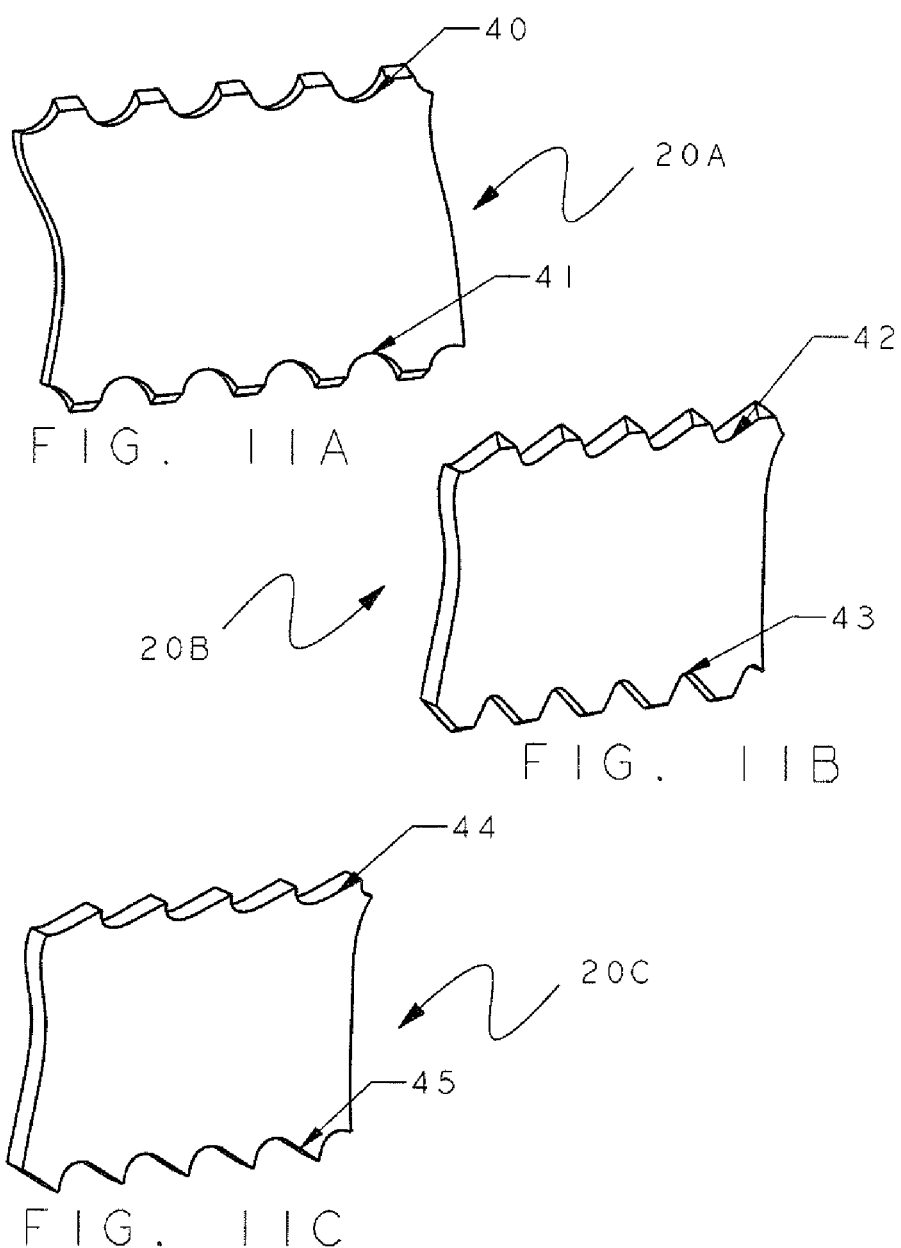
FIG. 11A is partial isometric view of an alternate contemplated tooth profile shape of the present implant shown in a partially flexed position.
FIG. 11B is partial isometric view of another alternate contemplated tooth profile shape of the present implant shown in a partially flexed position.
FIG. 11C is partial isometric view of still another alternate contemplated tooth profile shape of the present implant shown in a partially flexed position.

FIGS. 11A, 11B, and 11C are examples of alternate contemplated tooth profile shapes of the present implant, generally designated 20A, 20B, 20C, shown in a partially flexed position. In the preferred embodiment, the upper and lower tooth profiles 40 and 41 respectively, are teeth separated by semi-circular tooth pockets and can be formed such that the center points of the upper and lower tooth profiles are aligned or offset and staggered from each other. The tooth profile described above wherein alternate embodiments are provided with upper and lower symmetrical saw tooth shapes 42 and 43 which form a "v"-shaped tooth pocket or notch that is triangular in shape, or of upper and lower angled saw tooth shapes 44 and 45, or any combination thereof.

Figure 12:
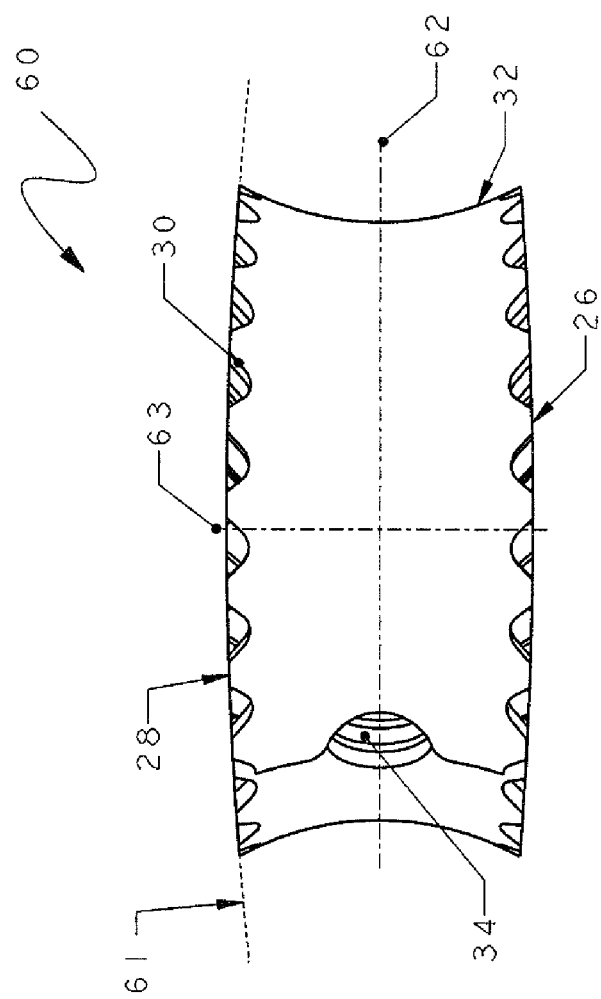
FIG. 12 is front plan view of an alternate embodiment of the present implant post-deployment.

FIG. 12 is an alternate embodiment of the present implant, generally designated 60 post-deployment. Components shared with the present implant 20 are designated with the identical reference numbers. The lower surface 26 and upper surface 28 are populated with geometry or teeth 30 used to increase pressure on the endplate of the vertebral body and prevent expulsion. It is contemplated that symmetric and asymmetric convex and segmented profiles 61 about a horizontal centerline 62 of surfaces 26 and 28 are also suitable for providing desired anatomical shapes, both regular and irregular.

The walls 32 of the implant 60 are concave and nest within each other for providing greater stability of the implant. It is also contemplated that symmetric and asymmetric curved and segmented wall shapes 32 about a vertical or axial centerline 63 are also suitable, both regular and irregular.

Figure 13:
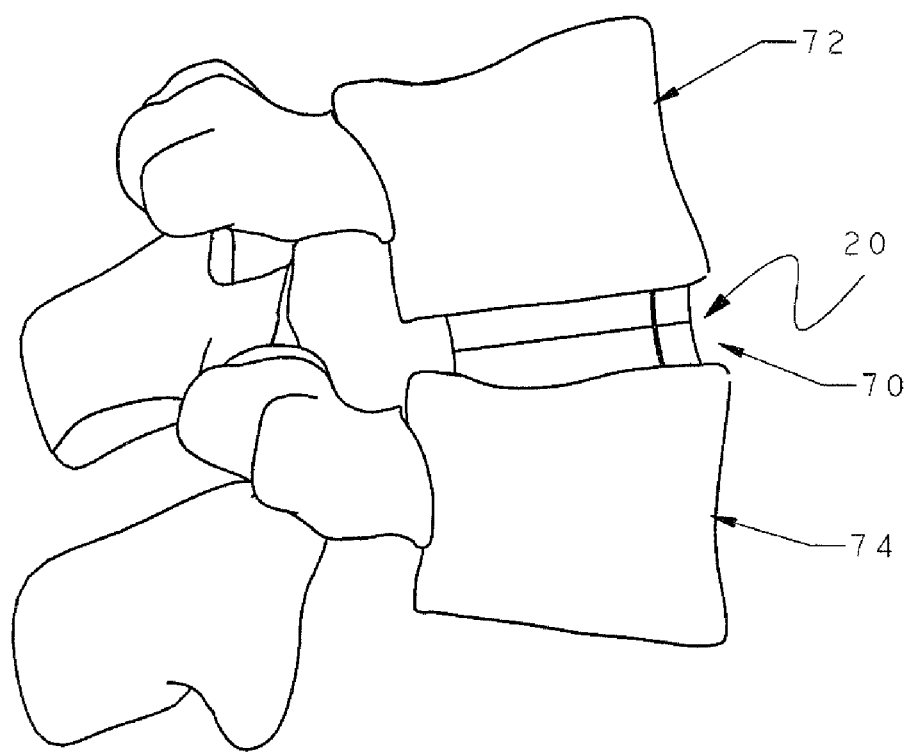
FIG. 13 is side plan view of the present implant situated intradiscal post-deployment.
Figure 14:
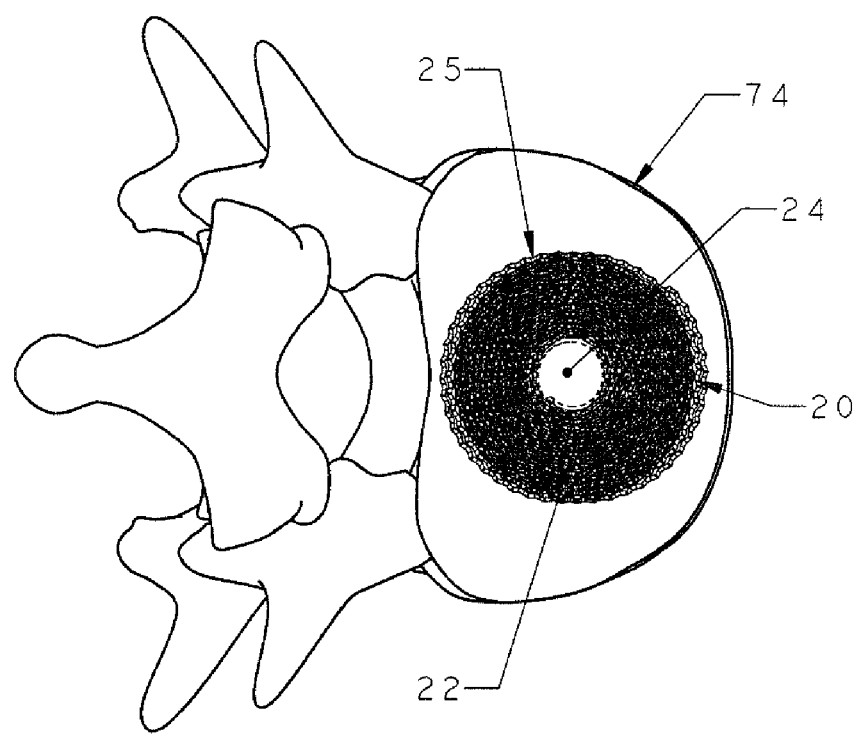
FIG. 14 is top plan view of the present implant situated intradiscal post-deployment.
Figure 15A:
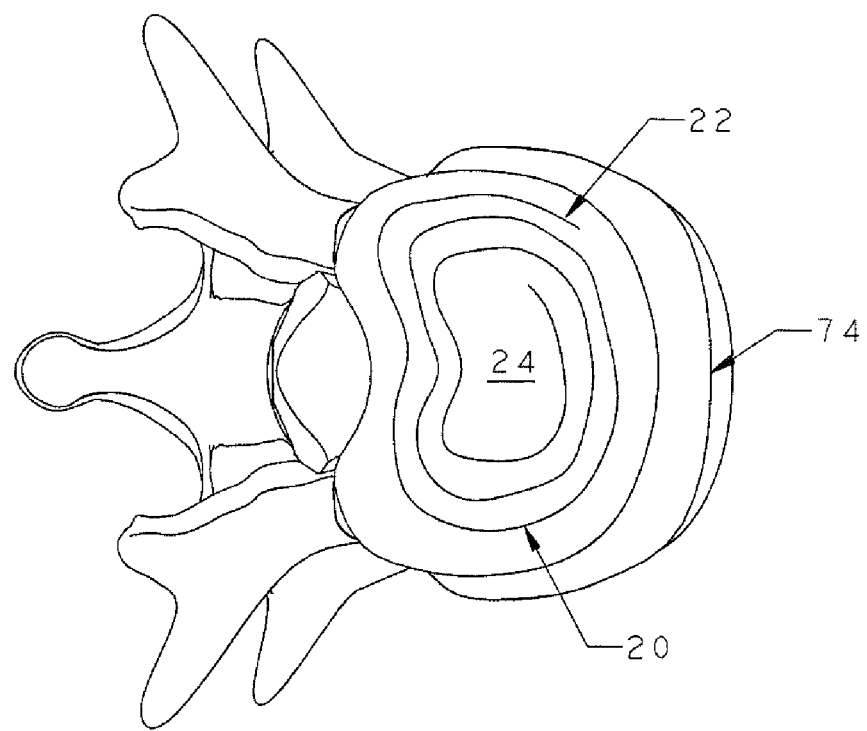
FIG. 15A is top plan view of an alternate contemplated embodiment of the present implant situated intradiscal post-deployment.
Figure 15B:
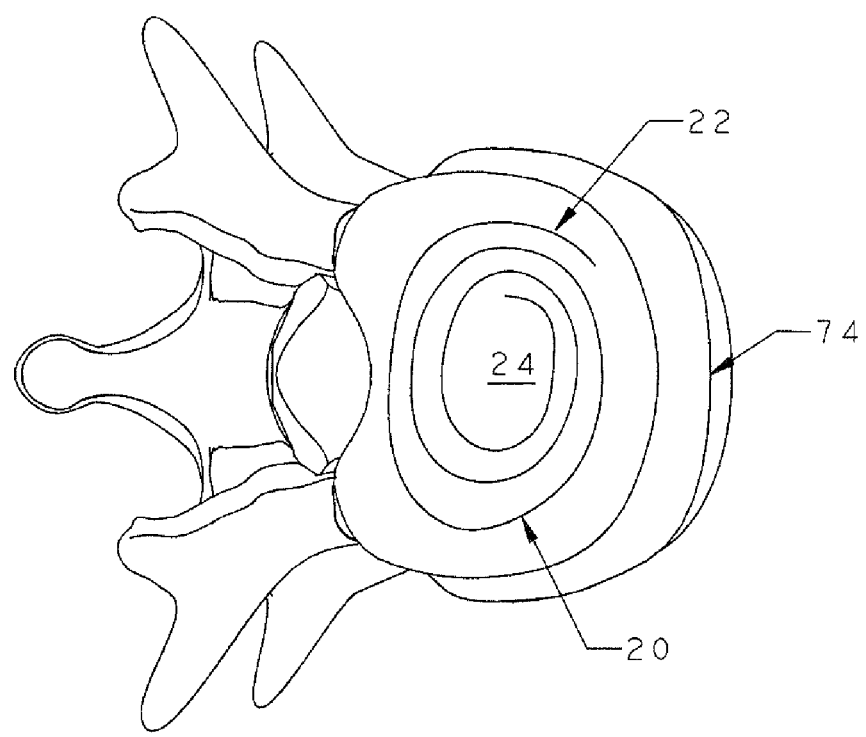
FIG. 15B is top plan view of an alternate contemplated embodiment of the present implant situated intradiscal post-deployment.
Figure 15C:
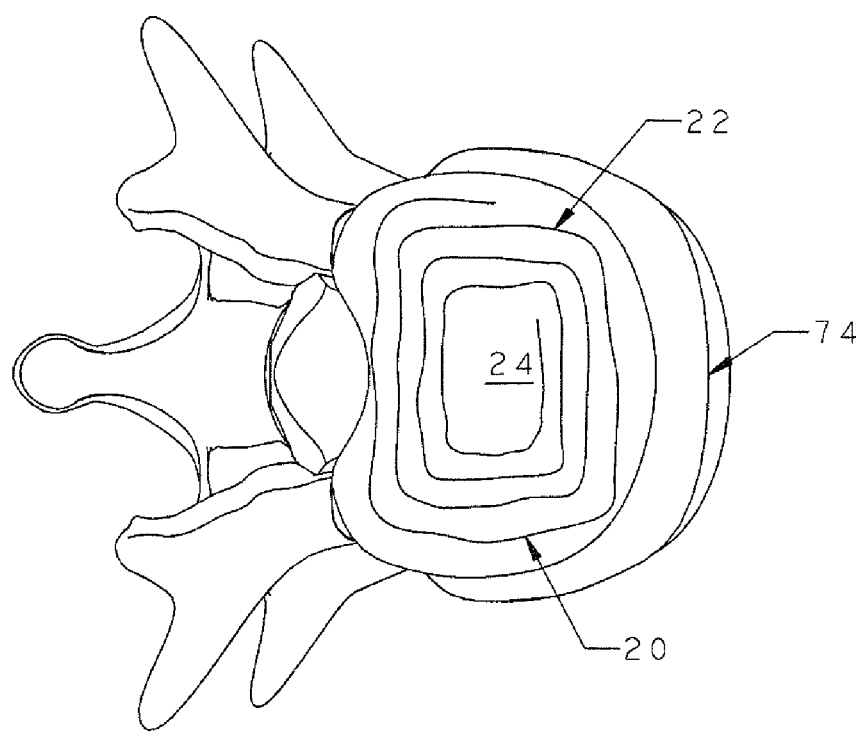
FIG. 15C is top plan view of an alternate contemplated embodiment of the present implant situated intradiscal post-deployment.
Figure 15D:
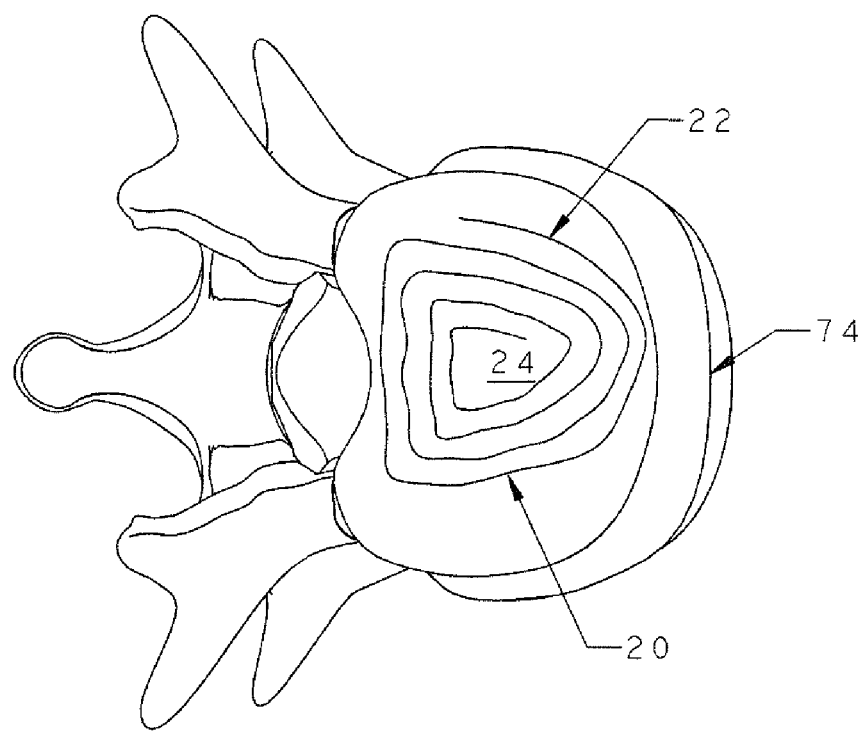
FIG. 15D is top plan view of an alternate contemplated embodiment of the present implant situated intradiscal post-deployment.

FIGS. 13 and 14 depict the present implant 20 post-deployment within a disc space 70 of the vertebral bodies 72 and 74. FIGS. 15A thru 15D are alternate embodiments of the present implant 20 formed into various suitable configurations of the spiral 22, when viewed from above, including but not limited to oval, triangular, square, pentagonal, hexagonal, cardioid, and other configurations of polygonal shapes, both regular and irregular. A transverse area of coverage depends on the chosen length of the pre-deployed implant 20, and how the implant is deployed. The surgeon can deploy the implant 20 in such a manner that both the passage 24 and the diameter 25 can be controlled and more closely matched with the anatomical features of the individual patient.

FIGS. 16 thru 23D illustrate various aspects of the pre-deployed implant, generally designated as 100. The pre-deployed implant 100 is an elongate strip that is generally cylindrical in shape as depicted in cross sectional FIG. 17C, but it is contemplated that other cross-sectional shapes are also suitable, including but not limited to oval, triangular, square, pentagonal, hexagonal and other configurations of polygonal shapes, both regular and irregular. Bend relief formations or cutouts 102 are spaced along the length of the strip and will be described in greater detail below. Edges of the strip are provided with linearly spaced teeth 103 in the form of circular cutouts.

Figure 8:
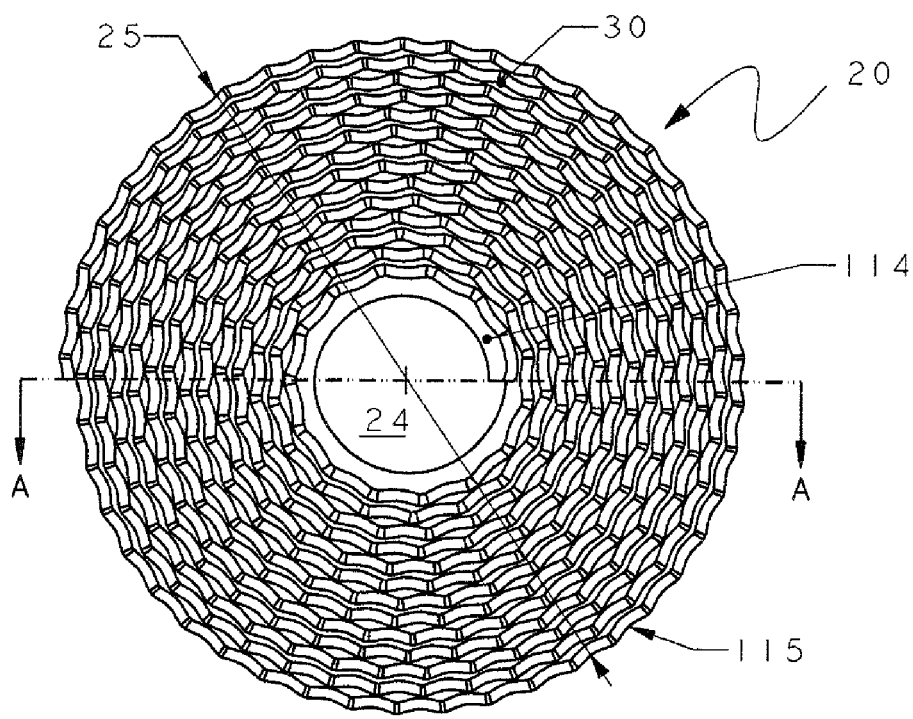
FIG. 8 is a top plan view of the present implant post-deployment.
Figure 8A:
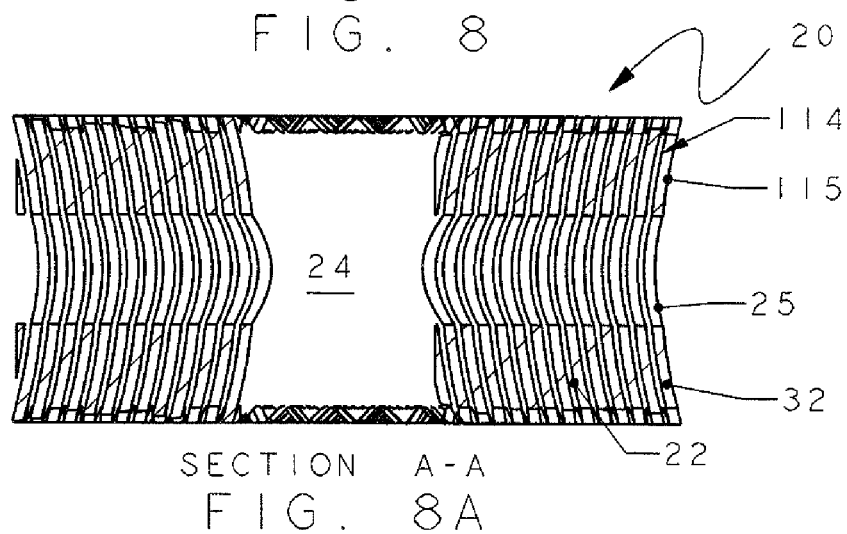
FIG. 8A is a vertical cross-section taken along the line A-A of FIG. 8 and in the direction indicated generally.
Figure 9:
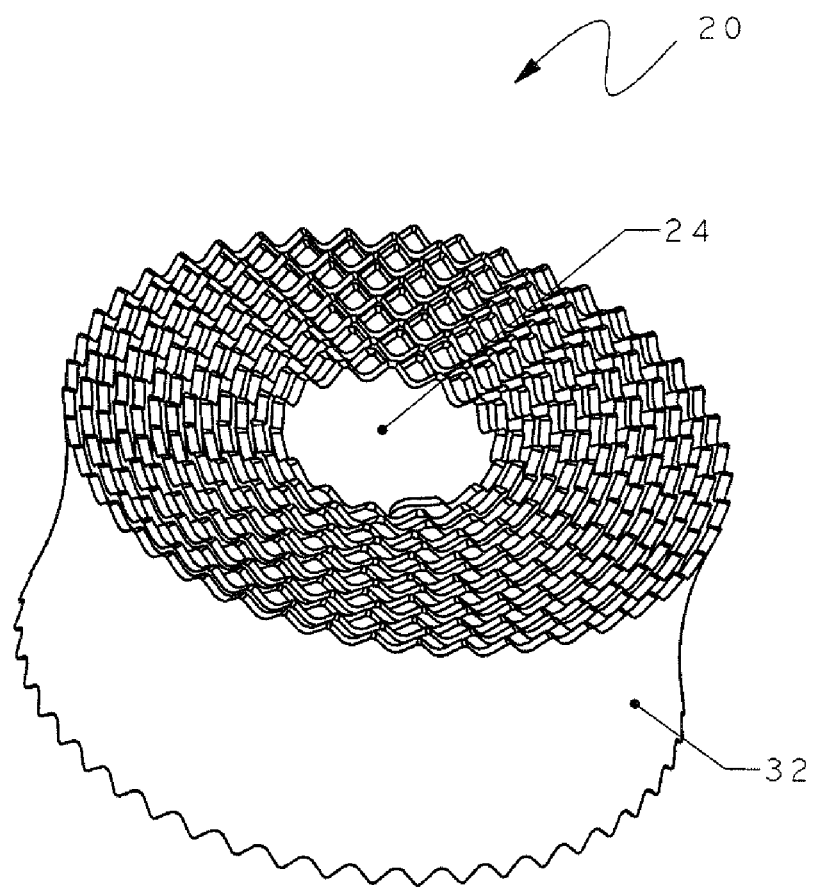
FIG. 9 is an isometric view of an alternate embodiment of the present implant post-deployment.
Figure 10:
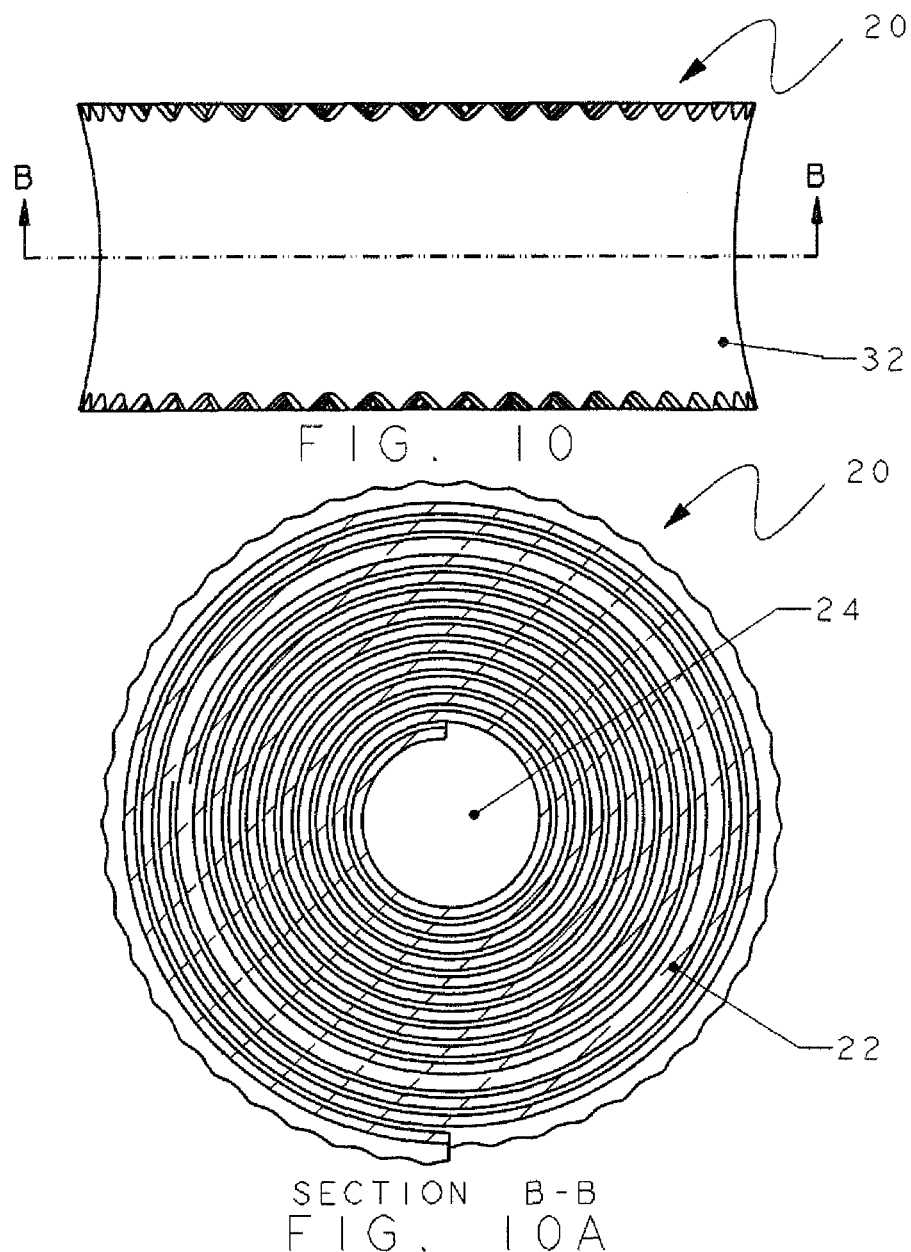
FIG. 10 is a front plan view of the present implant post-deployment.
Figure 22:
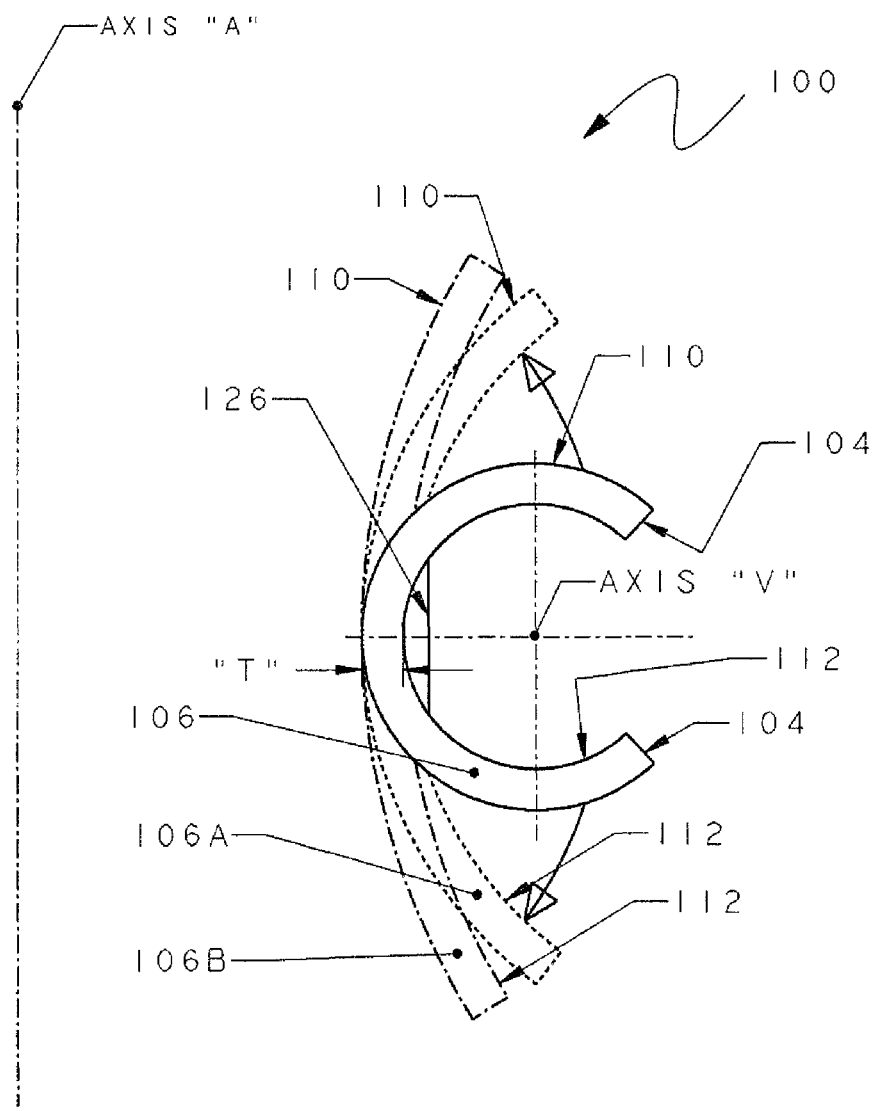
FIG. 22 is an enlarged vertical cross-section taken along the line B-B of FIG. 17 and in the direction indicated generally.

A break or slit 104 (FIGS. 17C, 17D) in the implant wall 106 causes the wall to transition from the main cylindrical shape defined by the wall 106 to alternate shapes 106a and 106b (shown in phantom in FIG. 22) as the implant 100 is wrapped around itself to form the spiral shape 22. This is achieved by bending an exterior of the wall 106 around an axis "A" perpendicular to a vertical axis "V" of the cylinder defined by the wall 106 and as depicted in FIG. 22. An interior surface 112 of the wall 106 as shown in FIG. 22 becomes the exterior wall 115 of the implant 20 as shown in FIG. 8A when fully deployed. The exterior surface 110 of the wall 106 becomes the interior wall 114 of the implant as depicted in FIG. 8A when fully deployed Implants of various heights can be provided by varying the amount of material removed from the cylindrical wall 106 to create the break or slit 104, depending on the desired final deployed height of the implant 20, 100. A larger break 104, meaning more material removed, will form a lower profile or shorter vertical deployed implant 20 that distracts the disc space 70, and a smaller break 104 will form a higher profile or taller vertical deployed implant that distracts the disc space as illustrated in FIG. 13. In use, the surgeon will be provided with a variety of implants 20, having different lengths and/or slit sizes.

A distal end 116 (FIG. 18) of the implant 100 is generally tapered on an angle cut perpendicular to the axis V of the implant. An opposite proximal end 118 (FIG. 18) generally defines the geometry of the desired final outer implant shape as depicted in FIGS. 15A thru 15D and is stiffer, in general, than the rest of the implant 100. This increased stiffness begins after an angular transition 120 located perpendicular to the axis "V" that transitions to a smaller cross sectional area by an increased break or slit 104 as shown in FIG. 17D. The preferred embodiment between the distal transition 120 and the proximal end 118 of the implant 100 has a generally thicker wall thickness "T" that is generally greater in size than the nominal implant wall thickness, thus providing a stiffer cross sectional area.

It is also contemplated that the present implant 100 is constructed using shape memory polymers or alloys, as is known in the art. In the preferred embodiment, the present implant 100 maintains a constant wall thickness "T" throughout the entire length from the proximal end 118 to the distal end 116, and the relative shapes and stiffness of portions of the implant are obtained thru the implant deployment process. The process of bending the implant 100 around itself and turning the interior surface 112 towards the exterior of the implant causes its original shape to form alternate shapes 106a and 106b, providing an activation force for the shape memory materials.

Preferred tooth profile shapes defined by the teeth 103 and the tooth pockets cut into the edge of the strip defining the break 104 of the present implant 100 are linearly spaced along the pre-deployed implant and are located at an edge formed by the intersection of the peripheral edge of the exterior 110 and the break or slit 104. The preferred embodiment maintains a constant distance "L" (FIG. 23) between each tooth 103, and the tooth pockets defining teeth 103 are spaced halfway between the locations of the bend relief geometry 102. This spacing ensures that the deployed teeth 30, 103 will be in line with each other as the spiral is wound around itself producing an un-aligned tooth pattern 122 as shown in FIG. 23A.

Figure 23:
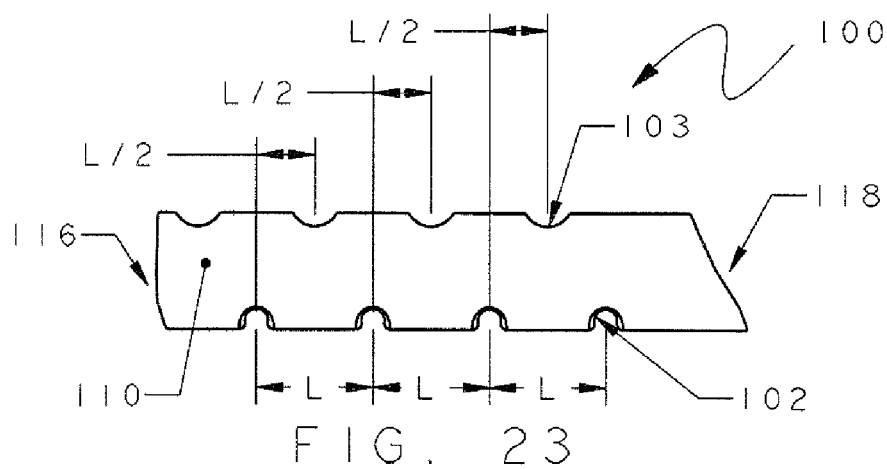
FIG. 23 is an enlarged fragmentary side view of the present implant pre-deployment.
Figure 23A:
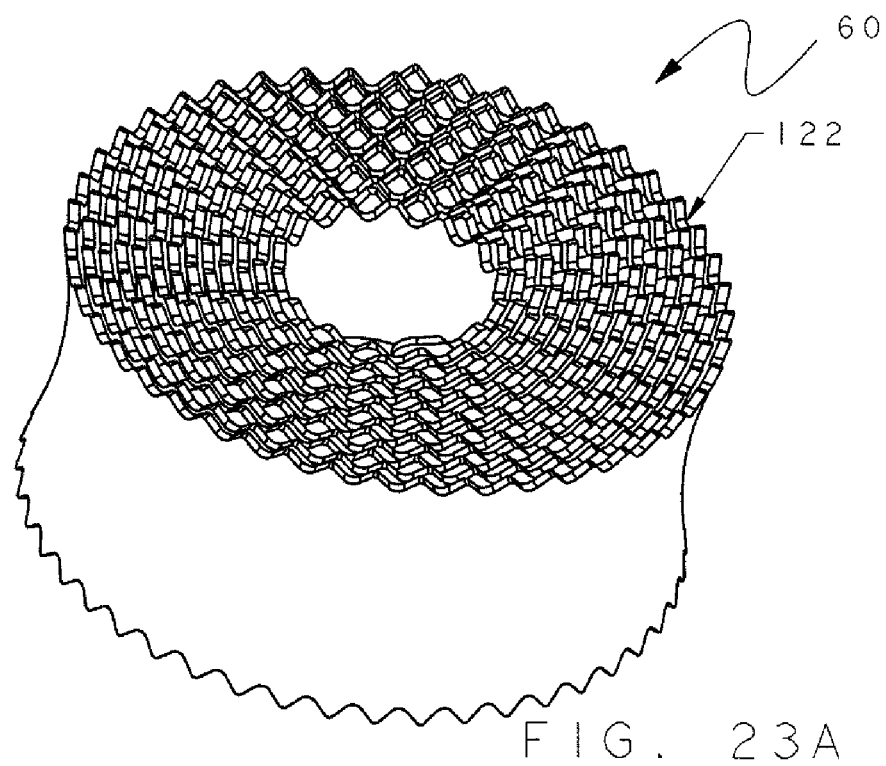
FIG. 23A is an isometric view of the present implant post-deployment.
Figure 23B:
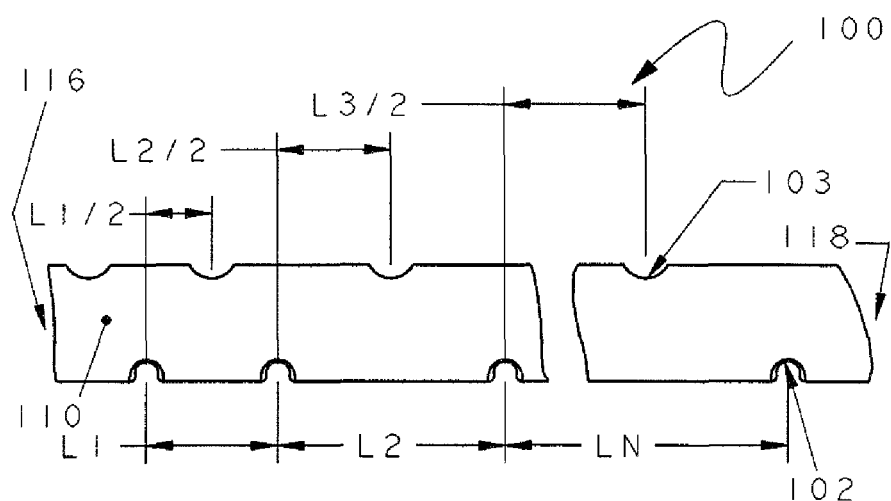
FIG. 23B is an enlarged side plan view of an alternate contemplated embodiment of the present implant pre-deployment.
Figure 23C:
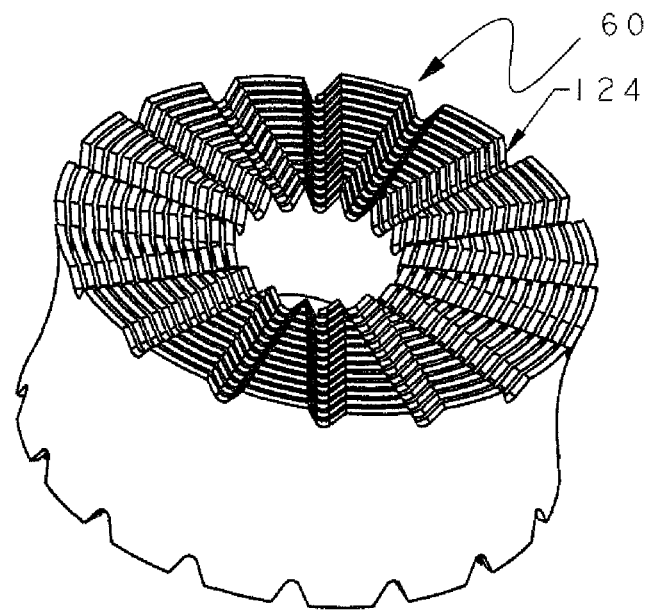
FIG. 23C is an isometric view of an alternate contemplated embodiment of the present implant post-deployment; [graph]
Figure 23D:
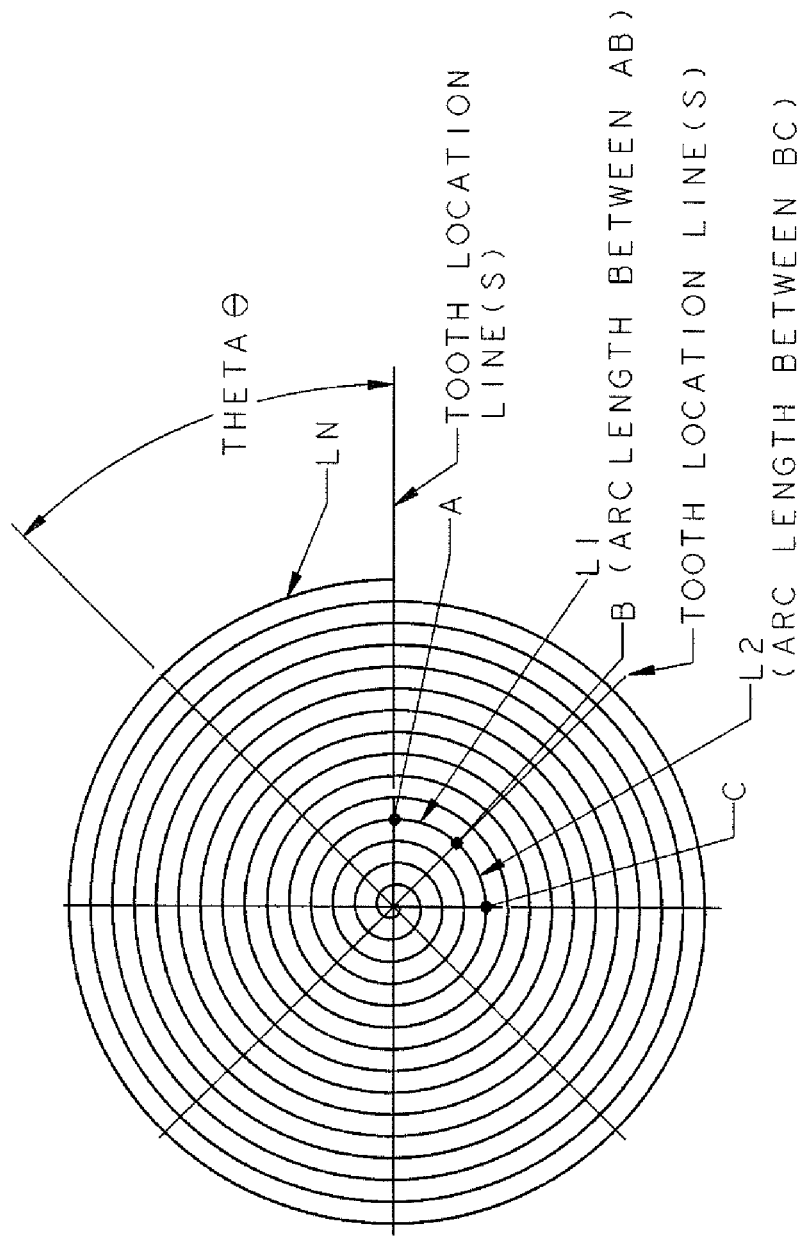
FIG. 23D is an isometric view of an alternate contemplated embodiment of the present implant post-deployment; [iso of implant]

Referring now to FIG. 23B thru 23D, an alternate spacing is depicted at $L_1$ thru $L_N$ of the bend relief geometry 102 and teeth 103 that is based on the arc length "L" of a polar spiral (T=a+bθ) given by the equation $$L = \frac{1}{2}b\left(\theta\sqrt{1+\theta^2} + \ln\left(\theta + \sqrt{1+\theta^2}\right)\right)$$

where θ is the angular dimension in radians between teeth 103 of a fully deployed spiral 22. The length $L_1$ thru $L_N$ between bend relief geometry 102 of an undeployed implant 100 will gradually increase from the proximal end 118 to the distal end 116. The location of the tooth pockets defining teeth 103 will also follow the same equation, and will always be spaced halfway between the bend relief geometry 102. This spacing ensures that the deployed teeth 30, 103 will be in line with each other as the spiral is wound around itself producing an aligned tooth pattern 124 as shown in FIG. 23C.

It is preferred that the teeth 30, 103 and the bend relief areas 102 are spaced linearly, such that as the spiral is formed as seen in FIG. 23A, the teeth and bend relief areas end up in somewhat of a random pattern (this being one embodiment). If the above-listed equation is used (second embodiment), then the teeth 30, 103, as well as the bend relief areas 102 will line up as the spiral takes shape as shown in 23C. The teeth 30, 103 will line up along "tooth location lines" (FIGS. 23C and 23D), and the bend relief areas 102 will line up along locations spaced at θ/2 (polar coordinates) or L/2 in linear dimensions. The distance defined as L/2 ($L_1/2$, $L_2/2$ .... $L_N/2$) between the teeth 30, 103 and the bend relief areas 102 ensures that the teeth will always be spaced halfway between the bend relief area as shown in FIGS. 23 thru 23D. It is also preferred that this arrangement is created so that any tooth 20, 103 and bend relief area 102 are never aligned with each other, resulting in a weakening of the structure. If $L_1/2=0$, then a specific tooth 103 and bend relief area 102 would be aligned, and a cross-section taken perpendicular to that location would be relatively weak.

Figure 30:
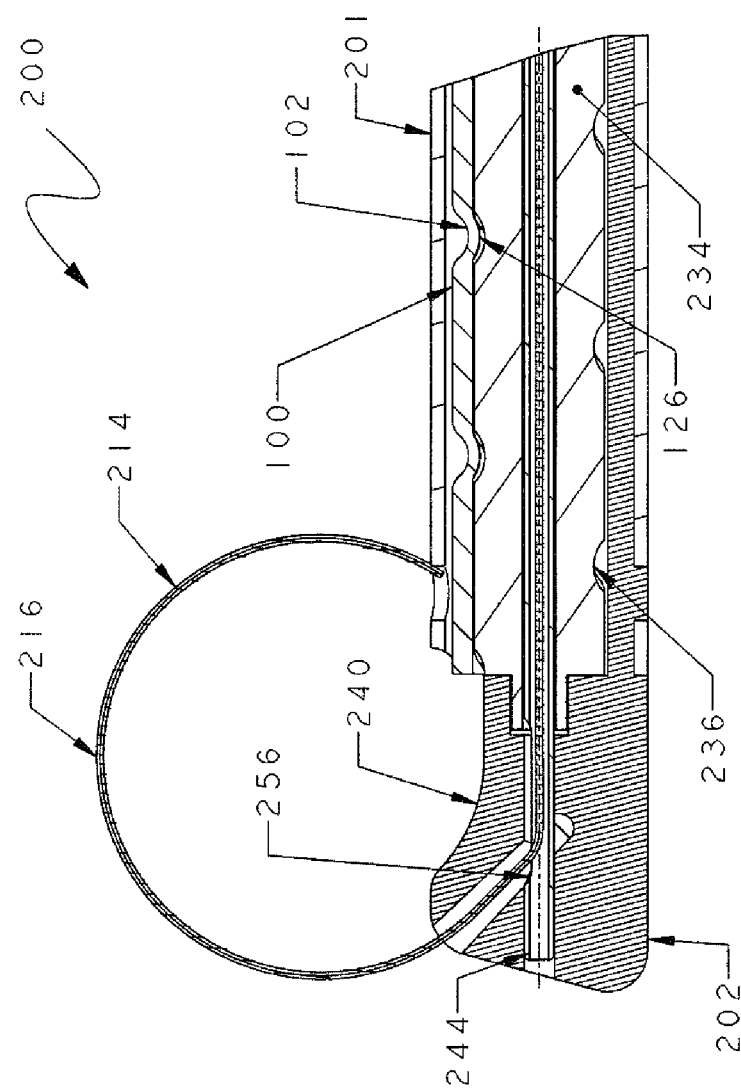
FIG. 30 is an enlarged vertical cross-section of the distal end of the implant delivery device.
Figure 31:
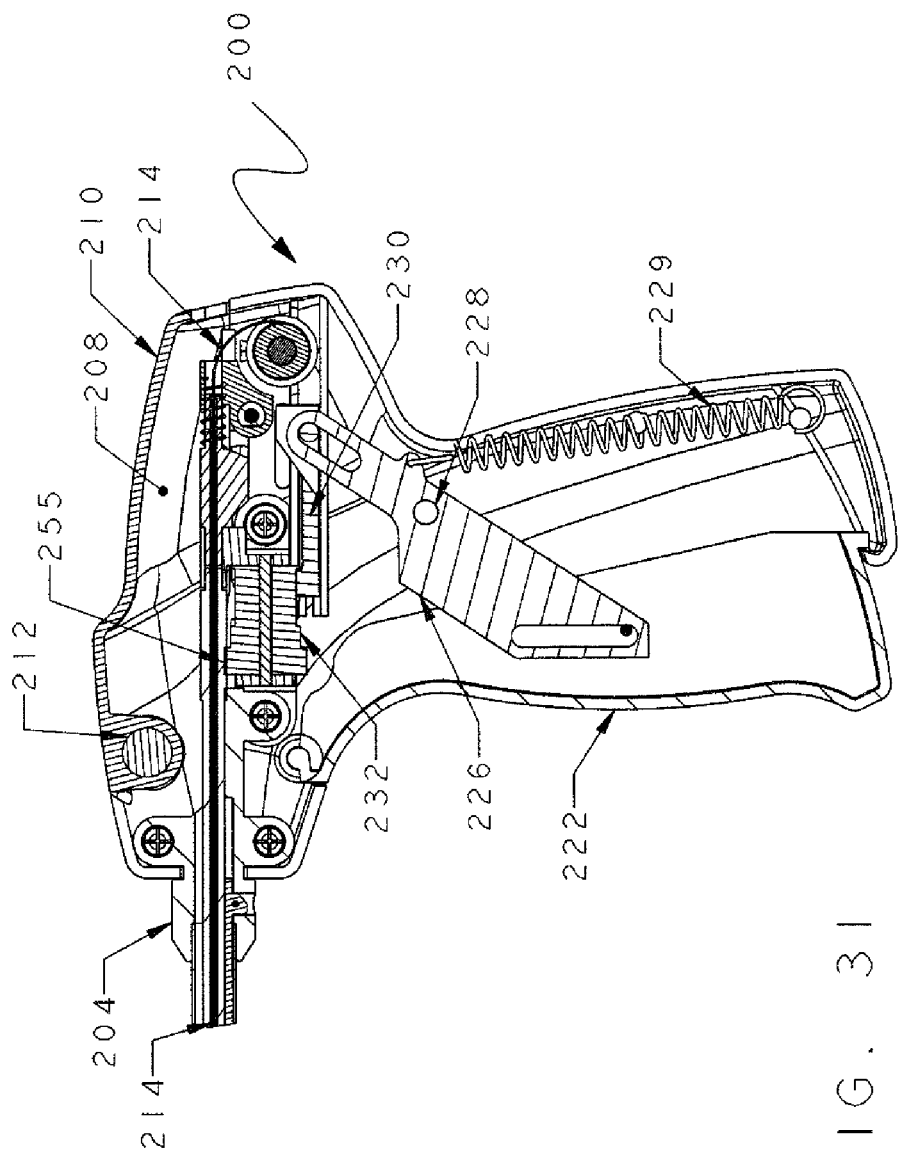
FIG. 31 is a vertical cross-section of the implant delivery device.

Referring now to FIG. 19, bend relief features 102 are generally semi-cylindrical or spherical concavities or dimples extending towards the interior and are formed from a portion of the exterior wall 110 of the pre-deployed implant 100. In the preferred embodiment, the bend relief features 102 are created by forming a cylindrical or spherical dimple or protrusion 126 that protrudes to the interior wall (FIG. 30). In essence, there should always be material, and never an opening in the cylinder wall where the bend relief features 102 are located. It is contemplated that other shapes are also suitable, including but not limited to oval, triangular, square, pentagonal, hexagonal and other configurations of polygonal extruded shapes, both regular and irregular.

Figure 17B:
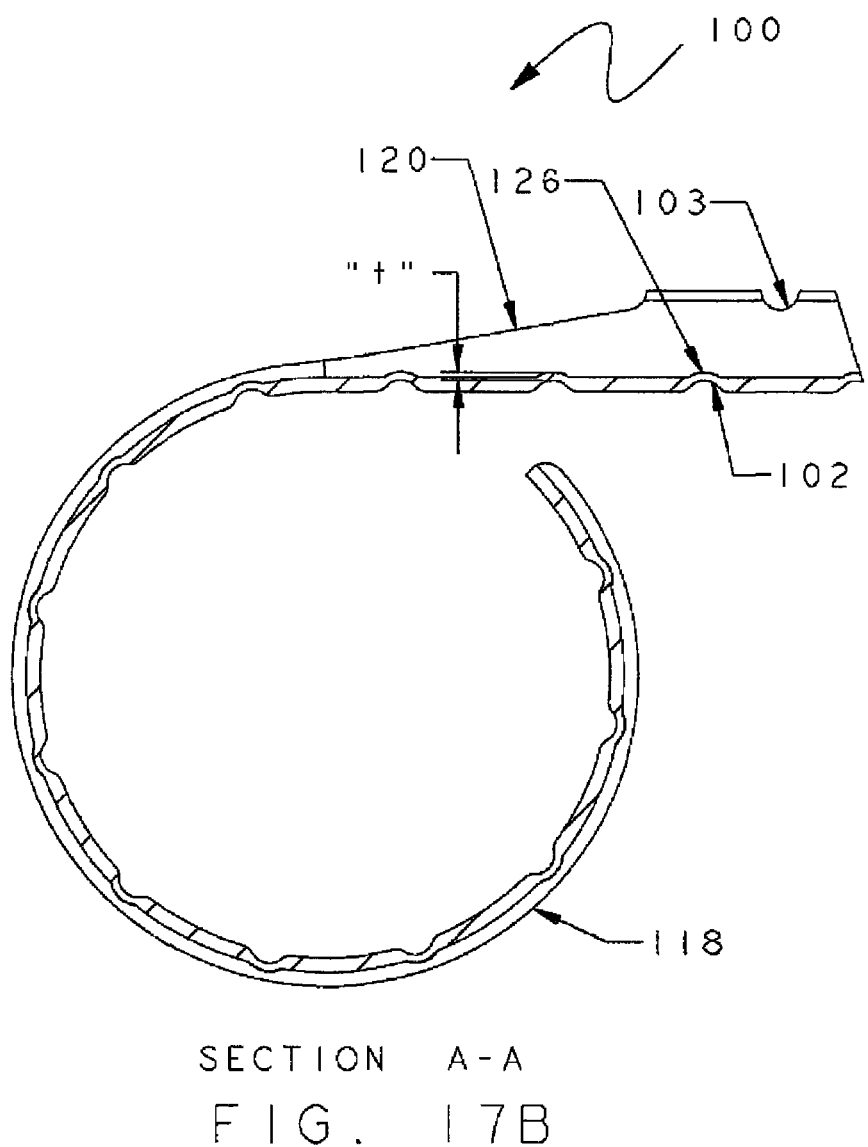
FIG. 17B is an enlarged fragmentary horizontal cross-section taken along the line A-A of FIG. 17 and in the direction indicated generally.
Figure 17C:
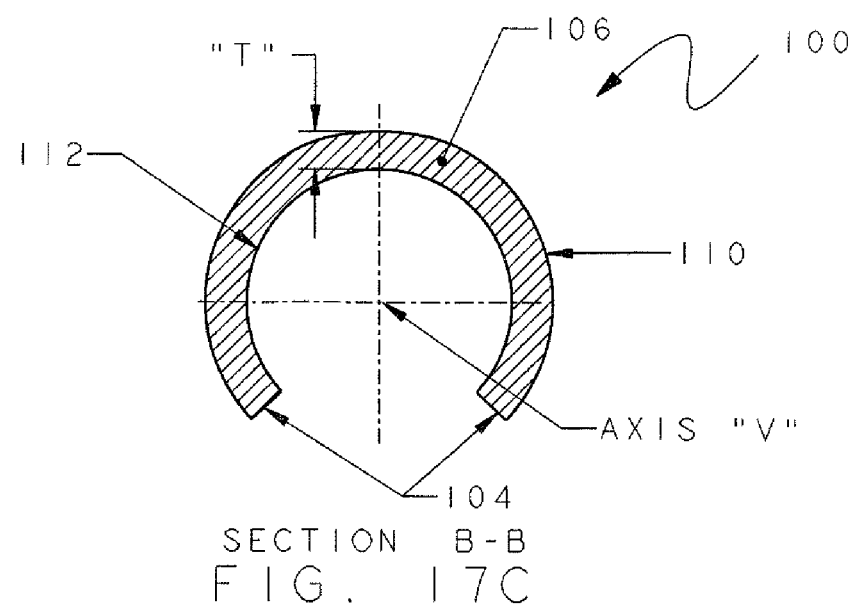
FIG. 17C is an enlarged vertical cross-section taken along the line B-B of FIG. 17 and in the direction indicated generally.
Figure 17D:
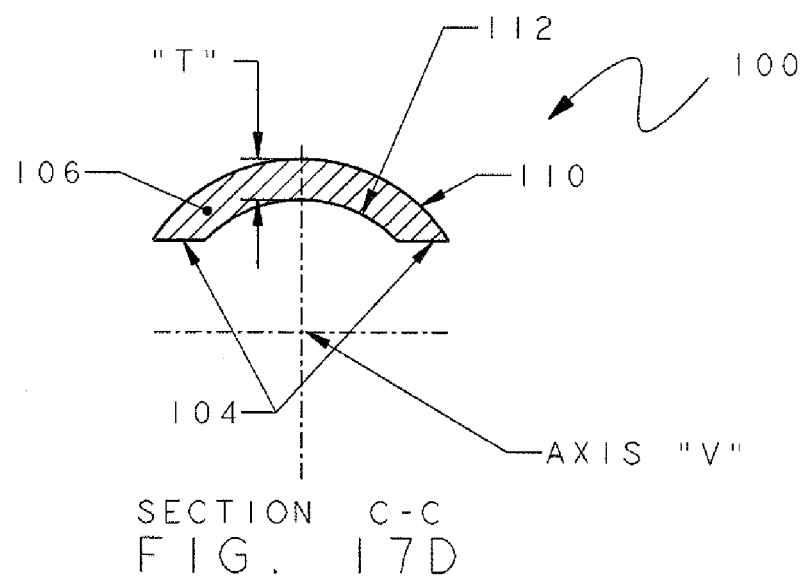
FIG. 17D is an enlarged vertical cross-section taken along the line C-C of FIG. 16 and in the direction indicated generally.
Figure 21:
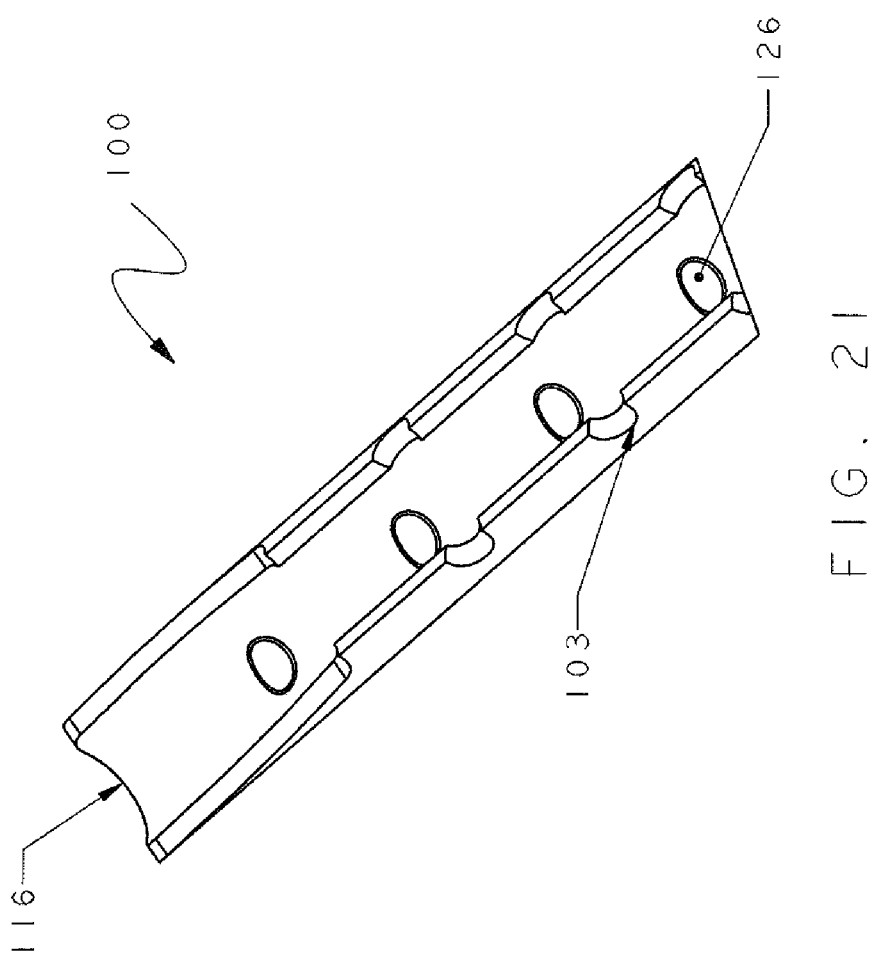
FIG. 21 is an enlarged isometric view of the distal end of the present implant pre-deployment.

As seen in FIG. 17B, bend relief features 102 have a smaller cross sectional wall thickness "t" than the nominal implant wall thickness ("T"). This decreased wall section allows an easier bend transition about the axis of the semi-cylindrical or spherical concavities. Aside from the bend relief formations, it is preferred that the implant 100 maintains a constant wall thickness "T" throughout the entire length. The process of bending the implant around itself and turning the interior surface 112 towards the exterior of the implant 100 provides an activation force for the shape memory materials.

Figure 24:
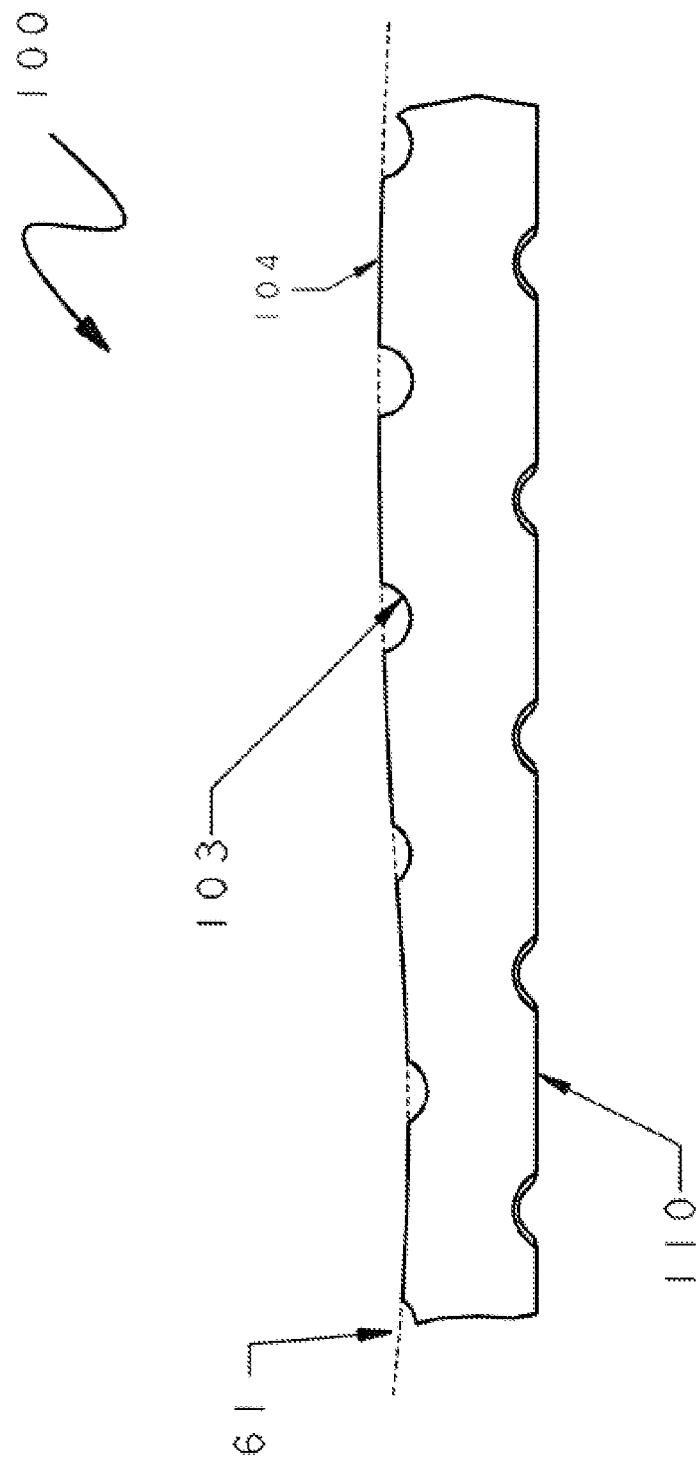
FIG. 24 is an enlarged side view of an alternate contemplated embodiment of the present implant pre-deployment.
Figure 25:
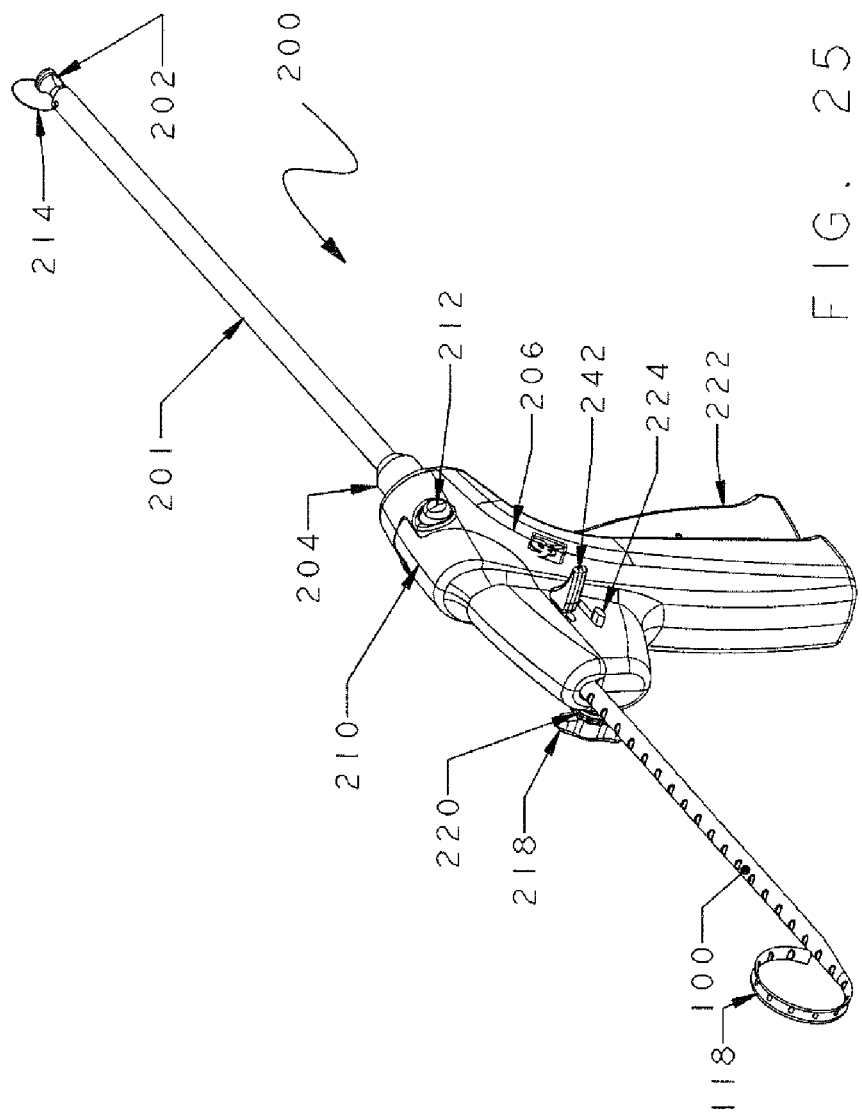
FIG. 25 is an isometric view of the present implant delivery device.
Figure 26:
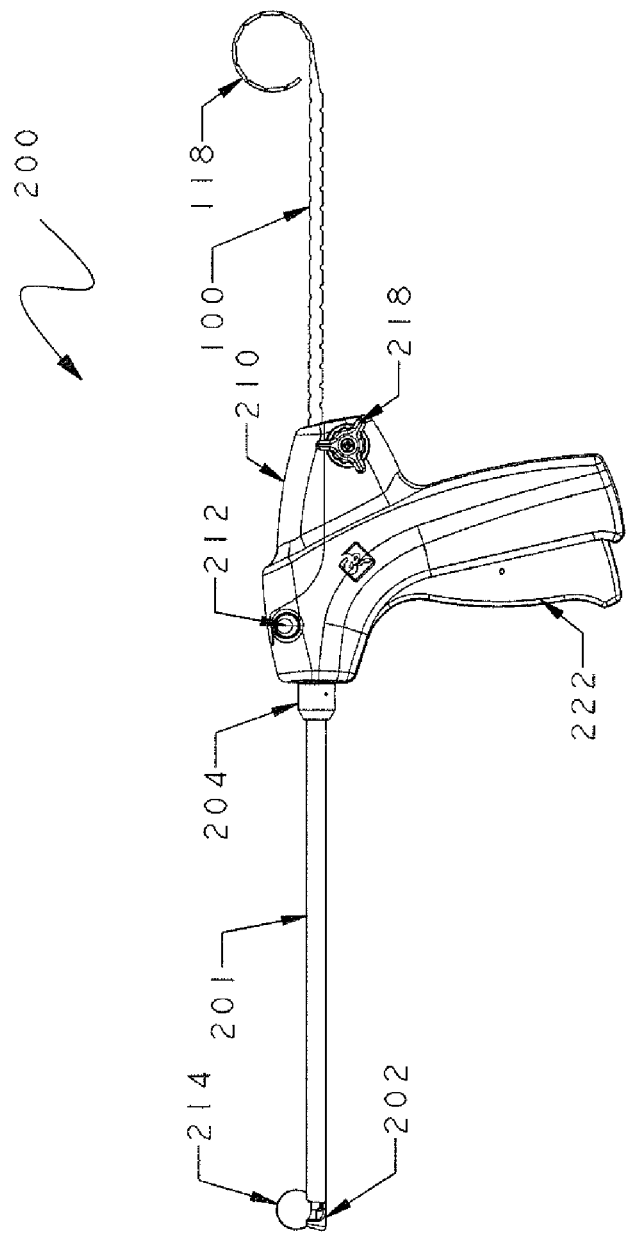
FIG. 26 is a front plan view of the present implant delivery device.
Figure 27:
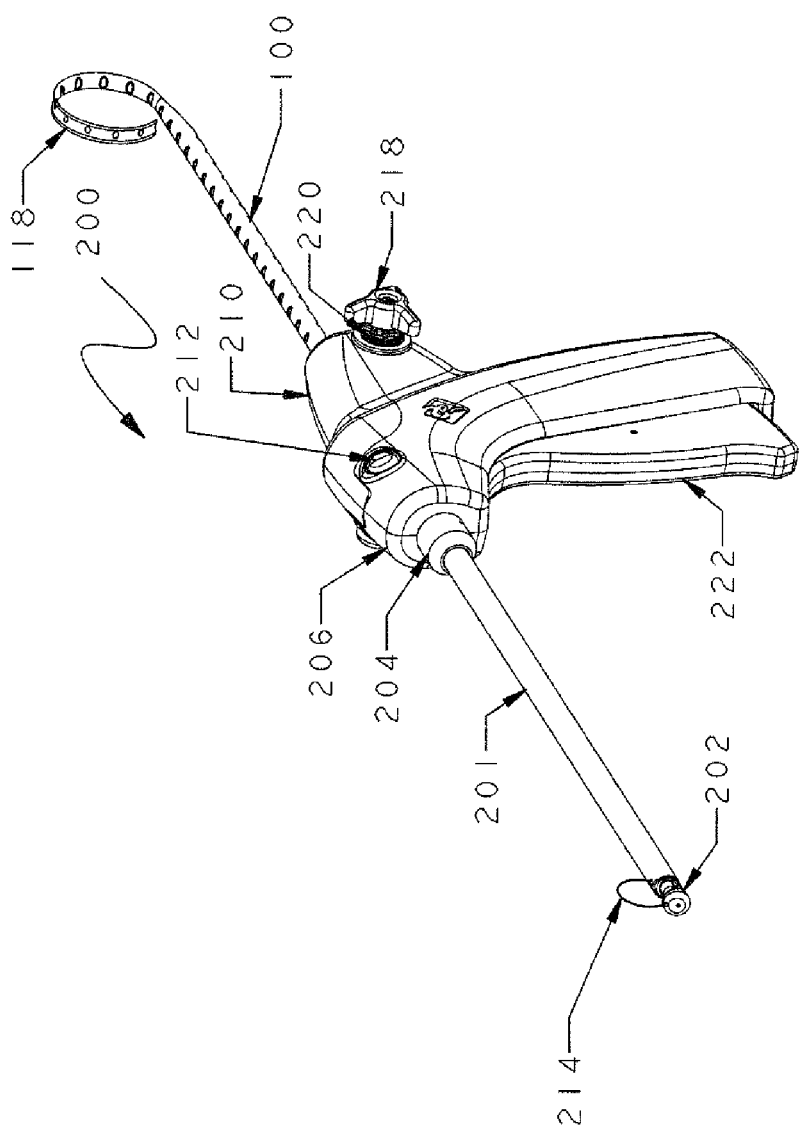
FIG. 27 is an isometric view of the present implant delivery device.

Referring now to FIG. 24, it is also contemplated that the break or slit 104 varies along the length of the pre-deployed implant 100, forming the lordotic or alternate profile 61 of surfaces 26 and 28 as illustrated in FIG. 12. The arcuate length of the break or slit 104 may vary along the length and may also be symmetric or asymmetric about the axis 'V' of the implant 100, causing surfaces 26 and 28 to have differing profiles 61.

Referring now to FIGS. 25 thru 32A, an implant delivery device is generally designated as 200. The delivery device 200 includes a delivery tube 201 which receives a fixed distal end deployment tip 202. At an opposite end, the delivery tube 201 is attached to a body collar 204 and the collar is screwed into a housing 206. An implant loading chamber 208 (FIG. 31) is located at an opposite end of the housing 206 from the delivery tube 201, and is accessed thru a door 210 by pressing a door release button 212. An implant tensioning cord 214 is preferably manufactured from Sulene-PET (polyethylene-terephthalate) or similar materials and is fed thru a centerline of the delivery device 200 defined by the delivery tube 201, and exits a distal end thru the deployment tip 202. A distal end of the tensioning cord 214 is attached to the delivery tube 201 creating the formation of a loop 216. A proximal end of the tensioning cord 214 is wound around a cord tensioning knob 218 and can be controlled by a variable tension adjustment mechanism 220.

Figure 29:
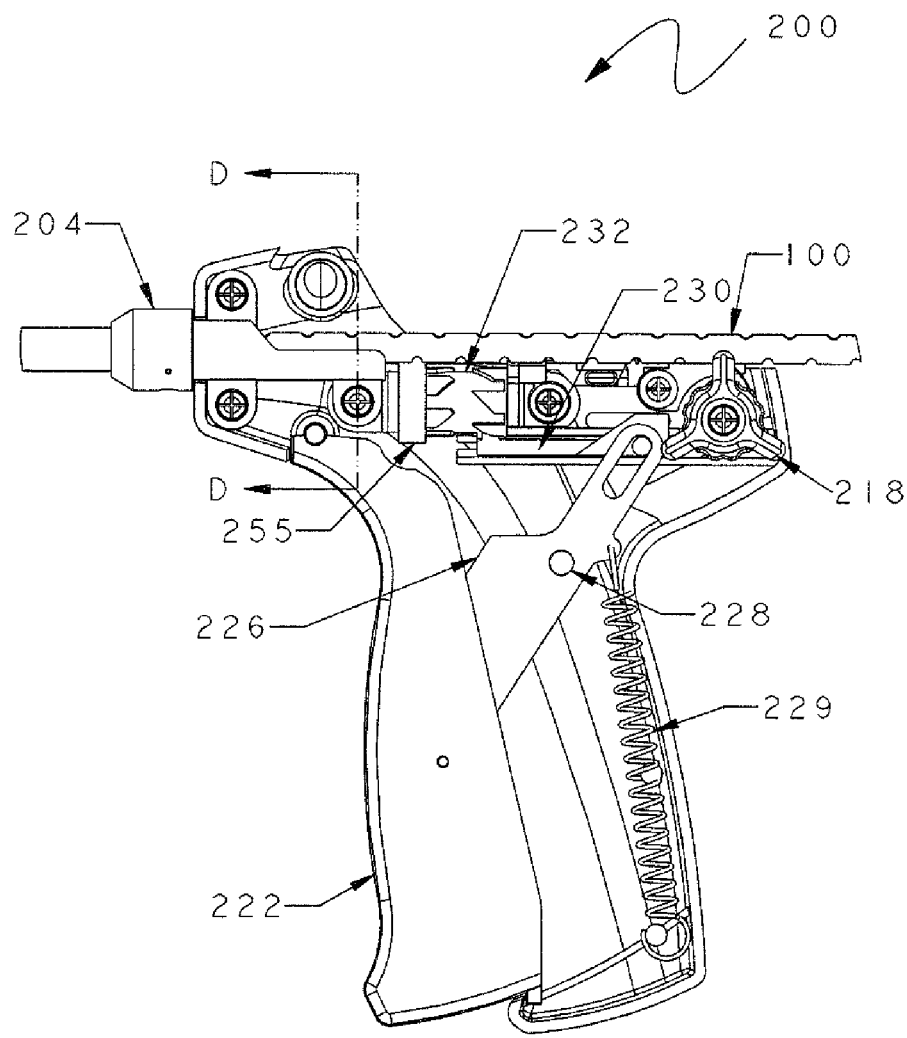
FIG. 29 is a front plan view of the implant delivery device of FIG. 25 with components removed for clarity.
Figure 29A:
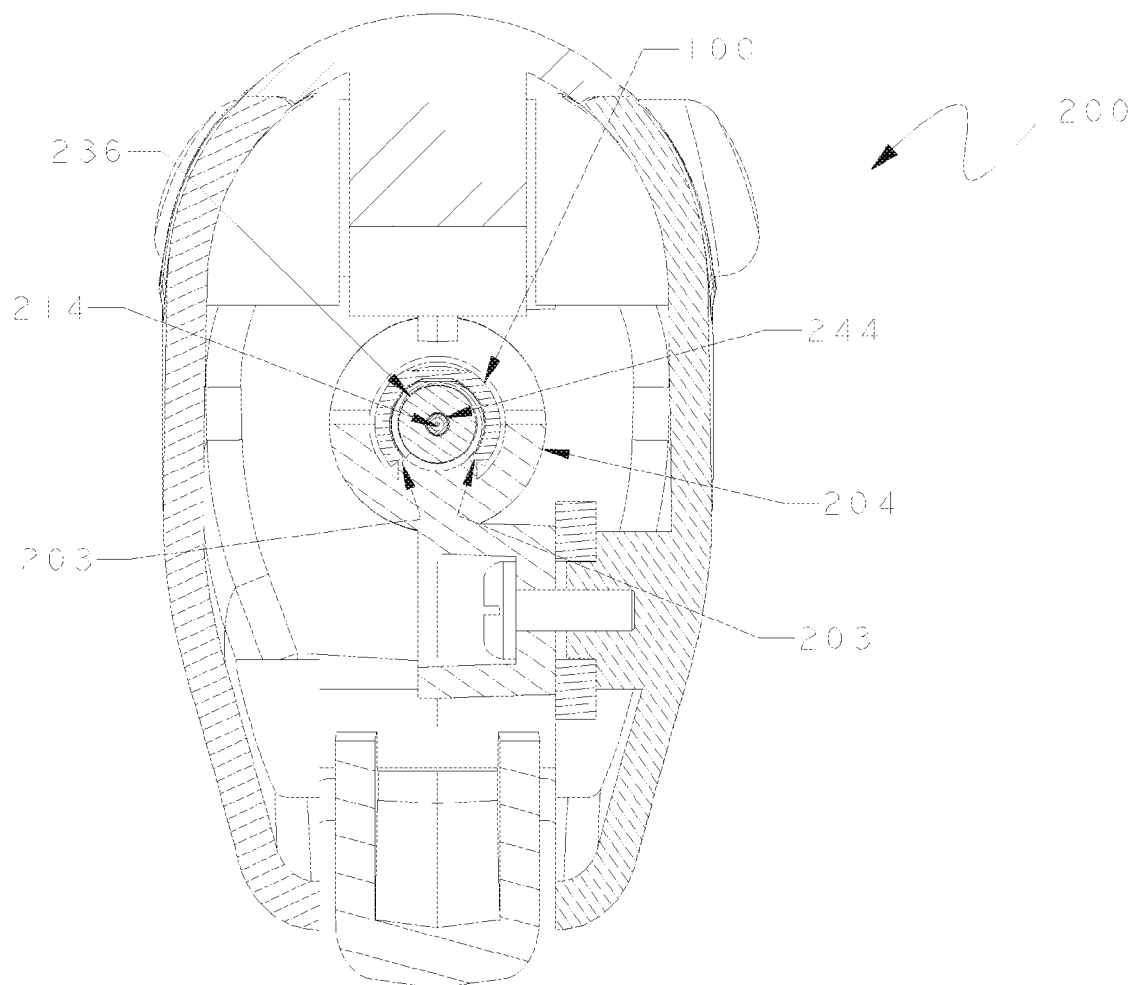
FIG. 29A is a cross section taken along the line D-D of FIG. 25 in the direction indicated generally with components removed for clarity of the implant delivery device.

Referring now to FIGS. 25, 29, 29A, 30, 32 and 32A, the implant 100 is loaded and oriented on rails 203 attached to the body collar 204 as shown in FIG. 29A. The purpose of the rails 203 is to orient the pre-deployed implant such that the break or slit 104 is facing downward. When a trigger 222 is pulled and released or the manual trigger over ride 224 is pushed forward and back, it actuates a trigger lever 226 which is held in position by a return spring 229 and a center post 228. The trigger lever 226 actuates a trigger slide 230 into a double acting cam mechanism 232 causing a clockwise rotation of the mechanism as seen from above the housing 206 (FIG. 29) The trigger slide 230 has a double-sided ramp 254 with an angled front surface 246 and an angled rear surface 248 (FIG. 32A).

When the trigger slide 230 moves forward, the angled front surface 246 acts upon a front ramp 250 attached to the cam mechanism 232, causing rotation of the cam mechanism. When the trigger 222 is released, the trigger slide 230 is forced backwards by the spring 229 and the trigger lever 226, causing the rear angled surface 248 to engage a rear ramp 252 of the cam mechanism 232, also causing rotation in the clockwise direction when viewed from the rear of the device as depicted in FIGS. 32 and 32A. Thus, each depression and release of the trigger 222 causes a double actuation of the cam mechanism 232. The rotation of the cam mechanism 232, through preferably frictional engagement between a relatively resilient ring 255 (FIGS. 29, 32 and 32A) and the Archimedes screw 234, preferably made of a rigid material such as stainless steel, causes counter-clockwise rotation of the Archimedes screw (FIGS. 30 and 32).

Figure 28:
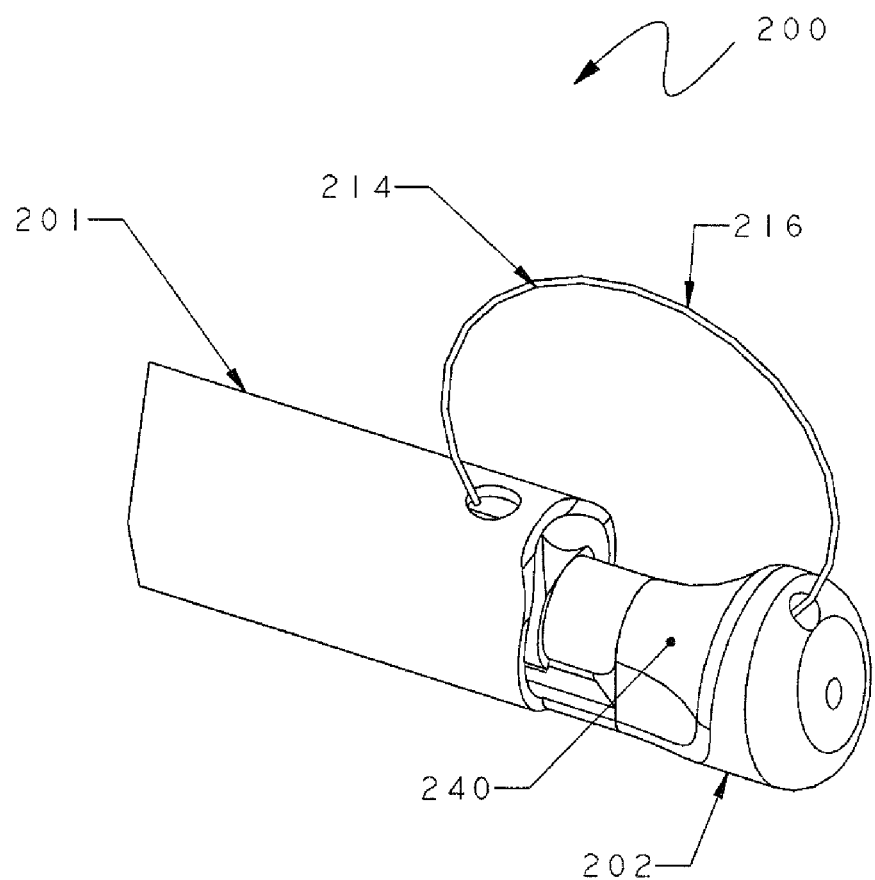
FIG. 28 is an enlarged isometric view of the distal end of the implant delivery device.

A reverse acting spline 236 which is a groove in the surface of the screw 234 interfaces with the bend relief features 102 of the implant 100, causing movement of the implant towards the distal end deployment tip 202. Thus, with each retraction of the trigger 222, the implant strip 100 is indexed towards the deployment tip 202. As seen in FIG. 28, the implant 100 rides within the tube 201 until it hits a flared ramp 240, forcing the implant break or slit 104 to open as depicted in FIG. 22 and change the concavity or arcuate cross-section of the implant 100. The implant 100 then hits the tensioning cord 214 and curls around the loop 216, creating the spiral shape 22. The trigger 222 is pulled and released until the implant 100 is fully deployed within the patient. Due to the relative stiffness of the curled proximal end 118, the curled shape of the implant 100 is maintained, since the proximal end forms the outermost surface of the implant and thus prevents uncoiling. Alternately, when shape memory polymers are used for the implant 100, the proximal end 118 has a memory of its curled shape and thus does not uncurl.

Referring now to FIG. 30, the tensioning cord 214 is cut post deployment by pulling back on a cord release lever 242, causing a cord knife 244, which reciprocates within the delivery tube 201, to move in such a manner that a sharp edge 256 of the knife 244 retracts backwards and severs the cord 214. The delivery device 200 can then be removed.

While a particular embodiment of the present in-situ formed spinal implant has been shown and described, it will be appreciated by those skilled in the art that changes and modifications may be made thereto without departing from the invention in its broader aspects and as set forth in the following claims.

What is claimed:

1. A device for installing a coiled elongate strip as a spinal implant, comprising:
    a housing having a delivery tube at one end, and an implant loading chamber at an opposite end;
    an indexing mechanism which moves the strip from said loading chamber to said delivery tube;
    a deployment tip being disposed in operational relationship to an end of said delivery tube, said deployment tip including a ramp for changing the concavity of the strip;
    a tensioning cord disposed in operational relationship to said deployment tip and forming a loop for causing the strip to form a coiled spiral upon progressive movement from said delivery tube; and,
    a splined screw rotating within said delivery tube for advancing the strip toward said deployment tip upon actuation of said trigger,
    wherein the elongate strip has a plurality of dimples extending towards an inner surface of the implant, and said splined screw has a helical groove constructed and arranged for accommodating the dimples for moving the implant through the device.

2. The device of claim 1 further comprising at least one rail disposed within said delivery tube and configured to orient the coiled elongated strip as the strip is moved through said delivery tube.

3. The device of claim 1 wherein the ramp comprises a first arc lying in a first plane, and a second arc lying in a second plane and being larger than said first arc, and said second arc disposed closer to said distal end than said first arc, each of said first and second planes being perpendicular to a longitudinal axis of the delivery tube.

4. A device for installing a coiled elongate strip as a spinal implant, comprising:
    a housing having a delivery tube at one end, and an implant loading chamber at an opposite end;
    an indexing mechanism which moves the strip from said loading chamber to said delivery tube;
    a deployment tip being disposed in operational relationship to an end of said delivery tube, said deployment tip including a flared ramp for changing the concavity of the strip;
    a tensioning cord disposed in operational relationship to said deployment tip and forming a loop for causing the strip to form a coiled spiral upon progressive movement from said delivery tube,
    wherein the flared ramp comprises a first arc lying in a first plane and a second arc lying in a second plane, said second arc being larger than said first arc, and said second arc disposed closer to said distal end than said first arc, each of said first and second planes being perpendicular to a longitudinal axis of the delivery tube.

5. The device of claim 4 further comprising at least one rail disposed within said delivery tube and configured to orient the coiled elongated strip as the strip is moved through said delivery tube.

6. The device of claim 4 further including a reciprocating knife disposed in said delivery tube and under operator control for severing said tensioning cord upon placement of said coiled implant.

7. The device of claim 4 further including a splined screw rotating within said delivery tube for advancing the strip toward said deployment tip upon actuation of said trigger.

8. The device of claim 7 wherein the elongate strip has a plurality of dimples extending towards an inner surface of the implant, and said splined screw has a helical groove constructed and arranged for accommodating the dimples for moving the implant through the device.

9. A device for installing a coiled elongate strip as a spinal implant, comprising:
    a housing having a delivery tube at one end, and an implant loading chamber at an opposite end;
    an indexing mechanism which moves the strip from said loading chamber to said delivery tube;
    a deployment tip being disposed in operational relationship to an end of said delivery tube, said deployment tip including a ramp for changing the concavity of the strip;
    a screw within said delivery tube configured to rotate and move the strip from said loading chamber to said deployment tip;
    a tensioning cord disposed in operational relationship to said deployment tip and forming a loop for causing the strip to form a coiled spiral upon progressive movement from said delivery tube; and,
    at least one rail disposed within said delivery tube and configured to orient the coiled elongated strip around said screw as the strip is moved through said delivery tube.

10. A device for installing a coiled elongate strip as a spinal implant, comprising:
    a housing having a delivery tube at one end, and an implant loading chamber at an opposite end;
    an indexing mechanism which moves the strip from said loading chamber to said delivery tube;

a deployment tip being disposed in operational relationship to an end of said delivery tube, said deployment tip including a ramp for changing the concavity of the strip;

a tensioning cord disposed in operational relationship to said deployment tip and forming a loop for causing the strip to form a coiled spiral upon progressive movement from said delivery tube; and, a reciprocating knife disposed in said delivery tube and under operator control for severing said tensioning cord upon placement of said coiled implant.

11. The device of claim 1 further including a splined screw rotating within said delivery tube for advancing the strip toward said deployment tip upon actuation of said trigger.

12. The device of claim 11 wherein the elongate strip has a plurality of dimples extending towards an inner surface of the implant, and said splined screw has a helical groove constructed and arranged for accommodating the dimples for moving the implant through the device.

13. The device of claim 1 further comprising at least one rail disposed within said delivery tube and configured to orient the coiled elongated strip as the strip is moved through said delivery tube.

* * * * *